US006632646B1

United States Patent
Aaslyng et al.

(10) Patent No.: US 6,632,646 B1
(45) Date of Patent: *Oct. 14, 2003

(54) MODIFIED SUBTILISINS AND DETERGENT COMPOSITIONS CONTAINING SAME

(75) Inventors: Dorrit Aaslyng, Roskilde (DK); Sven Branner, Lynaby (DK); Sven Hastrup, Copenhagen (DK); Leif Nørskov-Lauritsen, Tappernoje (DK); Ole Hvilsted Olsen, Brønshøj (DK); Merete Simonsen, Farum (DK); Eric Casteleijn, CG Capell a/d Ijssel (NL); Maarten Robert Egmond, GD Linschoten (NL); Johan Haverkamp, KL Bergschenhoek (NL); John David Marugg, BL Utrecht (NL); Arnoldus Theodorus Anthonius Mooren, TP Vlaardingen (NL)

(73) Assignees: Novozymes A/S, Bagsvaerd (DK); Unilever PLC., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/678,867

(22) Filed: Oct. 2, 2000

Related U.S. Application Data

(63) Continuation of application No. 08/815,775, filed on Mar. 12, 1997, now Pat. No. 6,197,567, which is a continuation of application No. 08/484,190, filed on Jun. 7, 1995, now Pat. No. 5,665,587, which is a continuation of application No. 07/776,115, filed on Oct. 15, 1991, now abandoned, which is a continuation-in-part of application No. 07/544,003, filed on Jun. 26, 1990, now abandoned, which is a continuation-in-part of application No. 07/516,026, filed on Apr. 26, 1990, now abandoned.

(30) Foreign Application Priority Data

Jun. 26, 1989 (DK) .............................. 3169/89
Jun. 26, 1989 (GB) .............................. 8914604
Jul. 7, 1989 (GB) .............................. 8915660

(51) Int. Cl.[7] .............................. C12N 9/50; C12N 9/54; C12N 15/57; C11D 3/386
(52) U.S. Cl. .............................. 435/220; 435/221; 435/222; 435/69.1; 435/252.31; 435/320.1; 435/471; 536/23.2; 510/300; 510/320
(58) Field of Search .............................. 435/69.1, 471, 435/220, 221, 252.31, 320.1, 222; 536/23.2

(56) References Cited

U.S. PATENT DOCUMENTS 4,760,025 A * 7/1988 Estell et al. .............. 510/392
4,914,031 A * 4/1990 Zukowski et al. .......... 435/222

(List continued on next page.)

FOREIGN PATENT DOCUMENTS

EP 0 260 105 A1 * 3/1988
EP 0 357 157 A1 * 3/1990

OTHER PUBLICATIONS

Cunningham et al., 1987, "Improvement in the alkaline stability of subtillisin using an efficient random mutagenesis and screening procedure", Protein Engineering, vol. 1, pp. 319–325.*

(List continued on next page.)

*Primary Examiner*—Ponnathapu Achutamurthy
*Assistant Examiner*—William W. Moore
(74) *Attorney, Agent, or Firm*—Elias J. Lambris

(57) ABSTRACT

Enzymes produced by mutating the genes for a number of subtilisin proteases and expressing the mutated genes in suitable hosts are presented.

The enzymes exhibit improved wash performance in comparison to their wild type parent enzymes.

The enzymes are well-suited for use in detergent compositions.

87 Claims, 5 Drawing Sheets

U.S. PATENT DOCUMENTS

| | | | | | |
|---|---|---|---|---|---|
| 4,980,288 | A | * | 12/1990 | Bryan et al. | 435/222 |
| 4,990,452 | A | * | 2/1991 | Bryan et al. | 435/222 |
| 5,013,657 | A | * | 5/1991 | Bryan et al. | 435/222 |
| 5,116,741 | A | * | 5/1992 | Bryan et al. | 435/87 |
| 5,118,623 | A | * | 6/1992 | Boguslawski et al. | 510/374 |
| 5,208,158 | A | * | 5/1993 | Bech et al. | 435/219 |
| 5,260,207 | A | * | 11/1993 | Pantoliano et al. | 435/221 |
| RE34,606 | E | * | 5/1994 | Estell et al. | 510/392 |
| 5,336,611 | A | * | 8/1994 | van Eekelen et al. | 435/221 |
| 5,397,705 | A | * | 3/1995 | Zukowski et al. | 435/222 |
| 5,399,283 | A | * | 3/1995 | Stabinsky et al. | 510/392 |
| 5,482,849 | A | * | 1/1996 | Branner et al. | 435/222 |
| 5,631,217 | A | * | 5/1997 | Branner et al. | 510/320 |
| 5,665,587 | A | * | 9/1997 | Aaslyng et al. | 435/221 |
| 5,700,676 | A | * | 12/1997 | Bott et al. | 435/221 |
| 5,741,694 | A | * | 4/1998 | Hastrup et al. | 435/222 |
| 5,837,517 | A | * | 11/1998 | Sierkstra et al. | 435/221 |
| 6,190,900 | B1 | * | 2/2001 | Sierkstra et al. | 435/221 |
| 6,197,567 | B1 | * | 3/2001 | Aaslyng et al. | 435/221 |
| 6,300,116 | B1 | * | 10/2001 | Von der Osten et al. | 435/220 |

OTHER PUBLICATIONS

Sternberg et al., 1987, "Prediction of electrostatic effects of engineering of protein charges", Nature, vol. 330, pp. 86–88.*

Thomas, P. G., et al., 1985, "Tailoring the pH dependence of enzyme catalysis using protein engineering", Nature, vol. 318, pp. 375–376.*

Estell et al., 1986, "Probing steric and hydrophobic effects on enzyme–substrate interactions by protein interactions by protein engineering", Science, vol. 233, pp. 659–663.*

Wells et al., 1987, "Designing substrate specificity by protein engineering of electrostatic interactions", Proceedings of the National Academy of Sciences, U.S.A., vol. 84, pp. 1219–1223.*

Russell et al., 1987, "Rational modification of enzyme catalysis by engineering surface charge", Nature, vol. 328, pp. 496–500.*

* cited by examiner

MODIFIED SUBTILISINS AND DETERGENT COMPOSITIONS CONTAINING SAME

CROSS-REFERENCE TO RELATED APPLICATIONS

This application is a continuation of U.S. application Ser. No. 08/815,775 filed on Mar. 12, 1997 now U.S. Pat. No. 6,197,567, which is a continuation of U.S. application Ser. No. 08/484,190 filed on Jun. 7, 1995 now U.S. Pat. No. 5,665,587, which is a continuation of U.S. application Ser. No. 07/776,115 filed on Oct. 15, 1991 now abandoned, which is a continuation-in-part of U.S. application Ser. No. 07/544,003 filed on Jun. 26, 1990 now abandoned, which is a continuation-in-part of U.S. application Ser. No. 07/516,026 filed on Apr. 26, 1990 now abandoned, and claims priority under 35 U.S.C. 119 of Danish application Ser. No. 3169/89 filed on Jun. 26, 1989, and Great Britain application Nos. 8914604.7 filed on Jun. 26, 1989, and 8915660.8 filed on Jul. 7, 1989, the contents of which are fully incorporated herein by reference.

FIELD OF THE INVENTION

This invention relates to novel mutant enzymes or enzyme variants useful in formulating detergent compositions in exhibiting improved wash performance, cleaning and detergent compositions containing said enzymes, mutated genes coding for the expression of said enzymes when inserted in a suitable host cell or organism and methods of selecting the amino acid residues to be changed in a parent enzyme in order to perform better in a given wash liquor under specified conditions.

BACKGROUND OF THE INVENTION

In the detergent industry, enzymes have been implemented in washing formulations for more than 20 years. Enzymes used in such formulations comprise proteases, lipases, amylases, cellulases, as well as other enzymes, or mixtures thereof. Commercially, proteases are most important.

Although proteases have been used in the detergent industry for more than 20 years, it is still not exactly known which physical or chemical characteristics are responsible for a good washing performance or ability of a protease.

The currently used proteases have been found by isolating proteases from nature and testing them in detergent formulations.

Bacillus Proteases

Enzymes cleaving the amide linkages in protein substrates are classified as proteases, or (interchangeably) peptidases (see Walsh, 1979, Enzymatic Reaction Mechanisms. W.H. Freeman and Company, San Francisco, Chapter 3). Bacteria of the Bacillus species secrete two extracellular species of protease, a neutral, or metalloprotease, and an alkaline protease which is functionally a serine endopeptidase, referred to as subtilisin. Secretion of these proteases has been linked to the bacterial growth cycle, with greatest expression of protease during the stationary phase, when sporulation also occurs. Joliffe et al. (1980, J. Bacterial 141:1199–1208) has suggested that Bacillus proteases function in cell wall turnover.

Subtilisin

A serine protease is an enzyme which catalyzes the hydrolysis of peptide bonds and in which there is an essential serine residue at the active site (White, Handler and Smith, 1973 "Principles of Biochemistry," Fifth Edition, McGraw-Hill Book Company, N.Y., pp. 271–272).

The bacterial serine proteases have molecular weights in the range of 20,000 to 45,000. They are inhibited by diisopropylfluorophosphate, but in contrast to metalloproteases, are resistant to ethylene diamino tetraacetic acid (EDTA) (although they are stabilized at high temperatures by calcium ions). They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest, 1977, Bacteriological Rev. 41:711–753).

In relation to the present invention a subtilisin is a serine protease produced by Gram-positive bacteria or fungi. A wide variety of subtilisins have been identified and the amino acid sequence of a number of subtilisins have been determined. These include at least six subtilisins from Bacillus strains, namely, subtilisin 168, subtilisin BPN', subtilisin Carlsberg, subtilisin DY, subtilisin amylosacchariticus and mesentericopeptidase (Kurihara et al., 1972, J. Biol. Chem. 247:5629–5631; Wells et al., 1983, Nucleic Acids Res. 11:7911–7925; Stahl and Ferrari, 1984, J. Bacteriol. 159:811–819, Jacobs et al., 1985, Nucl. Acids Res. 13:8913–8926; Nedkov et al., 1985, Biol. Chem. Hoppe-Seyler 366:421–430, Svendsen et al., 1986, FEBS Lett 196:228–232), one subtilisin from an actinomycetales, thermitase from Thermoactinomyces vulgaris (Meloun et al., 1985, FEBS Lett. 1983: 195–200) and one fungal subtilisin, proteinase K from Tritirachium album (Jany and Mayer, 1985, Biol. Chem. Hoppe-Seyler 366:584–492).

Subtilisins are well-characterized physically and chemically. In addition to knowledge of the primary structure (amino acid sequence) of these enzymes, over 50 high resolution X-ray structures of subtilisin have been determined which delineate the binding of substrate, transition state, products, at least three different protease inhibitors and define the-structural consequences for natural variation (Kraut, 1977, Ann. Rev. Biochem. 46:331–358).

In the context of this invention, a subtilisin variant or mutated subtilisin protease means a subtilisin that has been produced by an organism which is expressing a mutant gene derived from a parent microorganism which possessed an original or parent gene and which produced a corresponding parent enzyme, the parent gene having been mutated in order to produce the mutant gene from which said mutated subtilisin protease is produced when expressed in a suitable host.

Random and site-directed mutations of the subtilisin gene have both arisen from knowledge of the physical and chemical properties of the enzyme and contributed information relating to subtilisin's catalytic activity, substrate specificity, tertiary structure, etc. (Wells et al., 1987, Proc. Natl. Acad. Sci. U.S.A. 84; 1219–1223; Wells et al., 1986, Phil. Trans. R. Soc. Lond. A. 317:415–423: Hwang and Warshel, 1987, Biochem. 26:2669–2673; Rao et al., 1987, Nature 328:551–554).

Especially site-directed mutagenesis of the subtilisin genes has attracted much attention, and various mutations are described in the following patent applications and patents:

EP Publ. No. 130756 (GENENTECH) (corresponding to U.S. Pat. No. 4,760,025 (GENENCOR)) relating to site specific or randomly generated mutations in "carbonyl hydrolases" and subsequent screening of the mutated enzymes for various properties, such as $k_{cat}/k_m$ ratio, pH-activity profile and oxidation stability. Apart from revealing that site-specific mutation is feasible and that mutation of subtilisin BPN' in certain specified positions, i.e. $^{-1}$Tyr, $^{32}$Asp, $^{155}$Asn, $^{104}$Tyr, $^{222}$Met, $^{166}$Gly, $^{64}$His, $^{169}$Gly, $^{189}$Phe, $^{33}$Ser, $^{221}$Ser, $^{217}$Tyr, $^{156}$Glu or $^{152}$Ala, provide for enzymes exhibiting altered properties, this application does not contribute to solving the problem of deciding where to introduce mutations in order to obtain enzymes with desired properties.

EP Publ. No. 214435 (HENKEL) relating to cloning and expression of subtilisin Carlsberg and two mutants thereof. In this application no reason for mutation of $^{158}$Asp to $^{158}$Ser and $^{161}$Ser to $^{161}$Asp is provided.

In International Patent Publication No. WO 87/04461 (AMGEN) it is proposed to reduce the number of Asn-Gly sequences present in the parent enzyme in order to obtain mutated enzymes exhibiting improved pH and heat stabilities. In the application, emphasis is put on removing, mutating, or modifying the $^{109}$Asn and the $^{218}$Asn residues in subtilisin BPN'.

International patent publication No. WO 87/05050 (GENEX) discloses random mutation and subsequent screening of a large number of mutants of subtilisin BPN' for improved properties. In the application, mutations are described in positions $^{218}$Asn, $^{131}$Gly, $^{254}$Thr, $^{166}$Gly, $^{116}$Ala, $^{188}$Ser, $^{126}$Leu and $^{53}$Ser.

In EP Application No. 87303761 (GENENTECH) it is described how homology considerations at both primary and tertiary structural levels may be applied to identify equivalent amino acid residues whether conserved or not. This information together with the inventors' knowledge of the tertiary structure of subtilisin BPN' led the inventors to select a number of positions susceptible to mutation with an expectation of obtaining mutants with altered properties. The positions so identified are: $^{124}$Met, $^{222}$Met, $^{104}$Tyr, $^{152}$Ala, $^{156}$Glu, $^{166}$Gly, $^{169}$Gly, $^{189}$Phe, $^{217}$Tyr. Also $^{155}$Asn, $^{21}$Tyr, $^{22}$Thr, $^{24}$Ser, $^{32}$Asp, $^{33}$Ser, $^{36}$Asp, $^{46}$Gly, $^{48}$Ala, $^{49}$Ser, $^{50}$Met, $^{77}$Asn, $^{87}$Ser, $^{94}$Lys, $^{95}$Val, $^{96}$Leu, $^{107}$Ile, $^{110}$Gly, $^{170}$Lys, $^{171}$Tyr, $^{172}$Pro, $^{197}$Asp, $^{199}$Met, $^{204}$Ser, $^{213}$Lys and $^{221}$Ser. The positions are identified as being expected to influence various properties of the enzyme. In addition, a number of mutations are exemplified to support these suggestions. In addition to single mutations in these positions, the inventors also performed a number of multiple mutations. Furthermore, the inventors identified $^{215}$Gly, $^{67}$His, $^{126}$Leu, $^{135}$Leu and amino acid residues within the segments 97–103, 126–129, 213–215 and 152–172 as having interest, but mutations in any of these positions are not exemplified.

EP Publ. No. 260105 (GENENCOR) describes modification of certain properties in enzymes containing a catalytic triad by selecting an amino acid residue within about 15Å from the catalytic triad and replacing the selected amino acid residue with another residue. Enzymes of the subtilisin type described in the present specification are specifically mentioned as belonging to the class of enzymes containing a catalytic triad. In subtilisins, positions 222 and 217 are indicated as preferred positions for replacement.

International Patent Publication No. WO 88/06624 (GIST-BROCADES NV) discloses the DNA and amino acid sequences of a subtilisin protease designated PB92 which is almost 100% homologous to the amino acid sequence of Subtilisin 309.

International Patent Publication No. WO 88/07578 (GENENTECH) claims mutated enzymes derived from a precursor enzyme by replacement or modification of at least one catalytic group of an amino acid residue. The inventors state that by doing so a mutated enzyme is obtained that is reactive with substrates containing the modified or replaced catalytic group (substrate-assisted catalysis).

The general theory is based on *B. amyloliquefaciens* subtilisin (BPN'), where modifications have been described in positions $^{64}$His that was modified into $^{64}$Ala alone or in combination with a "helper" mutation of Ser-24-Cys. Modifications are also suggested in the amino acid residues $^{32}$Asp and $^{221}$Ser and a "helper" mutation of Ala-48-Glu.

International Patent Publication No. WO 88/08028 (GENEX) discloses genetic engineering around metal ion binding sites for the stabilization of proteins. This publication also uses Subtilisin BPN' as an example and points at the following amino acid residues as candidates for substitution $^{172}$Pro (P172D, P172E), $^{131}$Gly (G131D), $^{76}$Asn (N76D; N76D+P172D(E)), $^{78}$Ser (S78D). Further, suggestions are made for the combined mutants N76D+S78D+G131D+P172D(E); N76D+G131D; S78D+G131D; S78D+P172D(E) and S78D+G131D+P172D(E).

International Patent Publication No. WO 88/08033 (AMGEN) discloses a number of subtilisin analogues having a modified calcium binding site and either Asn or Gly replaced in any Asn-Gly sequence present in the molecule thereby obtaining enzymes exhibiting improved thermal and pH stability. One of the calcium binding sites is disclosed as involving the amino acid residues $^{41}$Asp, $^{75}$Leu, $^{76}$Asn, $^{77}$Asn, $^{78}$Ser, $^{79}$Ile, $^{80}$UGly, $^{81}$Val, $^{208}$Thr and $^{214}$Tyr; other potential calcium binding sites are suggested at $^{140}$Asp and $^{172}$Pro; $^{14}$Pro and $^{271}$Gln; and $^{172}$Pro and $^{195}$Glu or $^{197}$Asp. Also mutating the $^{109}$Asn and $^{218}$Asn positions is suggested. Mutants produced are N109S, N109S+N218S, N76D+N109S+N218S, N76D+N77D+N109S+N218S, N76D+I79E+N109S+N218S.

International Patent Publication No. WO 88/08164 (GENEX) describes a method for identifying residues in a protein which may be substituted by a cysteine to permit formation of potentially stabilizing disulfide bonds. The method is based on detailed knowledge of the three dimensional structure of the protein and uses a computer for selecting the positions. In relation to subtilisin proteases, Subtilisin BPN' was used as a model system. Using the method on Subtilisin BPN' resulted in the suggestion of 11 candidates for introducing disulfide bonds, i.e. 1:T22C+S87C, 2:V26C+L235C, 3:G47C+P57C, 4:M50C+N109C, 5:E156C+T164C, 6:V165C+K170C, 7:V165C+S191C, 8:Q206C+A216C, 9:A230C+V270C, 10:I234C+A274C and 11:H238C+W241C. Of these, four were produced, i.e. 1, 2, 4 and 8, of which two did not provide any stabilizing effect, i.e. 2 and 4. Further mutants were produced by combining two of these mutants with each other and one with another mutation, viz. T22C+S87C+N218S and T22C+S87C+Q206C+A216C. Also, a number of further unsuccessful mutants were produced, viz. A1C+S78C, S24C+S87C, K27C+S89C, A85C+A232C, I122C+V147C, S249C+A273C and T253C+A273C.

In addition, it has been shown by Thomas, Russell and Fersht, Nature 318, 375–376 (1985) that the exchange of $^{99}$Asp into $^{99}$Ser in subtilisin BPN' changes the pH dependency of the enzyme.

In a subsequent article J. Mol. Biol. 193, 803–813 (1987), the same authors discussed the substitution of $^{156}$Ser for $^{156}$Glu.

Both of these mutations are within a distance of about 15 Å from the active $^{64}$His.

In Nature 328, 496–500 (1987) Russel and Fersht discuss the results of their experiments and present rules for changing pH-activity profiles by mutating an enzyme to obtain changes in surface charge.

Isoelectric Point (pI$_o$)

The isoelectric point, pI$_o$, is defined as the pH value where the enzyme molecule complex (with optionally attached metal or other ions) is neutral, i.e. the sum of electrostatic charges. (net electrostatic charge=NEC) on the complex is equal to zero. In this sum of course consideration of the positive or negative nature of the individual electrostatic charges must be taken into account.

The isoelectric point is conveniently calculated by using equilibrium considerations using pK values for the various charged residues in the enzyme in question and then finding by iteration the pH value where the NEC of the enzyme molecule is equal to zero.

One problem with this calculation is that the pK values for the charged residues are dependent on their environment and consequently subject to variation. However, very good results are obtainable by allocating specific approximate pK values to the charged residues independently of the actual value. It is also possible to perform more sophisticated calculations, partly taking the environment into consideration.

The $pI_o$ may also be determined experimentally by isoelectric focusing or by titrating a solution containing the enzyme. In addition, the various pK values for the charged residues may be determined experimentally by titration.

Industrial Applications of Subtilisins

Proteases such as subtilisins have found much utility in industry, particularly in detergent formulations, as they are useful for removing proteinaceous stains.

At present, the following proteases are known, many of which are marketed in large quantities in many countries of the world:

Subtilisin BPN' or Novo, available from e.g. SIGMA, St. Louis, U.S.A.;

Subtilisin Carlsberg, marketed by Novo-Nordisk A/S (Denmark) as ALCALASE® and by IBIS (Holland) as MAXATASE®;

A *Bacillus lentus* subtilisin, marketed by NOVO INDUSTRI A/S (Denmark) as SAVINASE®;

Enzymes closely resembling SAVINASE® such as MAXACAL® marketed by IBIS and OPTICLEAN® marketed by MILES KALI CHEMIE (FRG);

A *Bacillus lentus* subtilisin, marketed by Novo Nordisk A/S (Denmark) as ESPERASE®; and KAZUSASE® marketed by SHOWA DENKO (Japan).

However, in order to be effective, these enzymes must not only exhibit activity under washing conditions, but also be compatible with other detergent components during detergent production and storage.

For example, subtilisins may be used in combination with other enzymes active against other substrates and, therefore, the selected subtilisin should possess stability towards and preferably should not catalyze the degradation of the other enzymes. In addition, the chosen subtilisin should be resistant to the action from other components in the detergent formulation, such as bleaching agents, oxidizing agents, etc., in particular an enzyme to be used in a detergent formulation should be stable with respect to the oxidizing power, calcium binding properties and pH conditions rendered by the non-enzymatic components in the detergent during storage and in the wash liquor during wash.

The ability of an enzyme to catalyze the degradation of various naturally occurring substrates present on the objects to be cleaned during e.g. wash is often referred to as its washing ability, washability, detergency or wash performance. Throughout this application the term wash performance will be used to encompass this property.

Naturally occurring subtilisins have been found to possess properties which are highly variable in relation to their washing power or ability under variations in parameters such as pH. Several of the above marketed detergent proteases, indeed, have a better performance than those marketed about 20 years ago, but for optimal performance each enzyme has its own specific conditions regarding formulation and wash conditions, e.g. pH, temperature, ionic strength (=I), active system (tensides, surfactants, bleaching agent, etc.), builders, etc.

As a result, it has been found that an enzyme possessing desirable properties at low pH and low I may be less attractive at more alkaline conditions and high I, or an enzyme exhibiting fine properties at high pH and high I may be less attractive at low pH, low I conditions.

The advent and development of recombinant DNA techniques has had a profound influence in the field of protein chemistry.

It has been envisaged that these techniques will make it possible to design peptides and proteins, such as enzymes and hormones according to desired specifications, enabling the production of compounds exhibiting desired properties.

It is now possible to construct enzymes having desired amino acid sequences, and as indicated above a fair amount of research has been devoted to designing subtilisins with altered properties. The proposals include the technique of producing and screening a large number of mutated enzymes as described in EP Publ. No. 130756 (GENENTECH) (U.S. Pat. No. 4,760,025 (GENENCOR)) and International patent Publ. No. WO 87/05050 (GENEX). These methods correspond to the classical method of isolating native enzymes and screening them for their properties, but is more efficient through the knowledge of the presence of a large number of different mutant enzymes.

Since a subtilisin enzyme typically comprises 275 amino acid residues each capable of being 1 out of 20 possible naturally occurring amino acids, one very serious drawback in that procedure is the very large number of mutations generated that has to be submitted to a preliminary screening prior to further testing of selected mutants showing interesting characteristics at the first screening, since no guidance is indicated in determining which amino acid residues to change in order to obtain a desired enzyme with improved properties for the use in question, such as, in this case formulating detergent compositions exhibiting improved wash performance under specified conditions of the wash liquor.

A procedure as outlined in these patent applications will consequently only be slightly better than the traditional random mutation procedures which have been known for years.

The other known techniques relate to changing specific properties, such as transesterification and hydrolysis rate (EP Publ. No. 260105 (GENENCOR)), pH-activity profile (Thomas, Russell and Fersht, supra) and substrate specificity (International Patent Publ. No. WO 88/07578 (GENENTECH)). None of these publications relates to changing the wash performance of enzymes.

A further technique that has evolved is using the detailed information on the three dimensional structure of proteins for analyzing the potential consequences of substituting certain amino acids. This approach is described in EP 260105 (GENENCOR), WO 88/07578 (GENENTECH), WO 88/08028 (GENEX), WO 88/08033 (AMGEN) and WO 88/08164 (GENEX).

Thus, as indicated above, no relationship has yet been identified between well defined properties of an enzyme such as those mentioned above and the wash performance of an enzyme.

In unpublished International Patent Application No. PCT/DK 88/00002 (NOVO INDUSTRI A/S), it is proposed to use the concept of homology comparison to determine which amino acid positions should be selected for mutation and which amino acids should be substituted in these positions in order to obtain a desired change in wash performance.

By using such a procedure the task of screening is reduced drastically, since the number of mutants generated is much smaller, but with that procedure it is only foreseen that enzymes exhibiting the combined useful properties of the parent enzyme and the enzyme used in the comparison may be obtained.

The problem seems to be that although much research has been directed at revealing the mechanism of enzyme activity, still only little is known about the factors in structure and amino acid residue combination that determine the properties of enzymes in relation to their wash performance.

Consequently, there still exists a need for further improvement and tailoring of enzymes to wash systems as well as a better understanding of the mechanism of protease action in the practical use of cleaning or detergent compositions. Such an understanding could result in rules which may be applied for selecting mutations that with a reasonable degree of certainty will result in an enzyme exhibiting improved wash performance under specified conditions in a wash liquor.

Lipases in Detergents

Examples of known lipase-containing detergent compositions are provided by EP 0 205 208 and 0 206 390 (Unilever), which relate to lipases derived from Ps. fluorescens, P gladioli and Chromobacter in detergent compositions.

EP 0 214 761 (Novo) and EP 0 258 068 (Novo) give a detailed description of lipases from certain microorganisms and disclose the use thereof in detergent additives and detergent compositions. The lipases disclosed in EP 0 214 761 are derived from organisms of the species Pseudomonas cepacia. The lipases disclosed in EP 0 258 068 are derived from organisms of the genus Thermomyces/Humicola.

A difficulty with the simultaneous incorporation of both lipases and proteases into such compositions is that the protease tends to attach the lipase.

Measures have been proposed to mitigate this disadvantage.

One such attempt is represented by EP 0 271 154 (Unilever) wherein certain selected proteases with an isoelectric point of less than 10 are shown to combine advantageously with lipases.

Another attempt is described in WO 89/04361 (Novo) which concerns detergent compositions containing lipase derived from Pseudomonas and protease derived from Fusarium or protease of a subtilisin type which has been mutated in its amino acid sequence at position 166, 169 or 222 in certain ways. It was reported that there was some reduction in the degree of attack upon the lipase by the particular proteases described.

| ABBREVIATIONS | | |
|---|---|---|
| AMINO ACIDS | | |
| A = | Ala = | Alanine |
| V = | Val = | Valine |
| L = | Leu = | Leucine |
| I = | Ile = | Isoleucine |
| P = | Pro = | Proline |
| F = | Phe = | Phenylalanine |
| W = | Trp = | Tryptophan |
| M = | Met = | Methionine |
| G = | Gly = | Glycine |
| S = | Ser = | Serine |
| T = | Thr = | Threonine |
| C = | Cys = | Cysteine |
| Y = | Tyr = | Tyrosine |
| N = | Asn = | Asparagine |
| Q = | Gln = | Glutamine |
| D = | Asp = | Aspartic Acid |
| E = | Glu = | Glutamic Acid |
| K = | Lys = | Lysine |
| R = | Arg = | Arginine |
| H = | His = | Histidine |
| NUCLEIC ACID BASES | | |
| A = | | Adenine |
| G = | | Guanine |
| C = | | Cytosine |
| T = | | Thymine (only in DNA) |
| U = | | Uracil (only in RNA) |

Mutations

In describing the various mutants produced or contemplated according to the invention, the following nomenclatures were adapted for ease of reference: Original amino acid(s) position(s) substituted amino acid(s).

Accordingly, the substitution of Glutamic acid for glycine in position 195 is designated as:

Gly 195 Glu or G195E.

A deletion of glycine in the same position is designated as:

Gly 195 * or G195* and an insertion of an additional amino acid residue such as lysine is designated as:

Gly 195 GlyLys or G195GK.

Where a deletion is indicated in Table I or present in a subtilisin not indicated in Table I, an insertion in such a position is indicated as:

* 36 Asp or *36D for insertion of an aspartic acid in position 36.

Multiple mutations are separated by pluses, i.e.:

Arg 170 Tyr+Gly 195 Glu or R170Y+G195E representing mutations in positions 170 and 195 substituting tyrosine and glutamic acid for arginine and glycine, respectively.

TABLE I

COMPARISON OF AMINO ACID SEQUENCE FOR VARIOUS PROTEASES a = subtilisin BPN' (Wells et al, 1983, supra)
b = subtilisin amylosaccharificus (Kurihara et al, 1972, supra)
c = subtilisin 168 (Stahl and Ferrari, 1984, supra)
d = subtilisin mesentericopeptidase (Svendsen et al, 1986, supra)
e = subtilisin DY (Nedkov et al, 1985, supra)
f = subtilisin Carlsberg (Smith et al, 1968, supra)
g = subtilisin Carlsberg (Jacobs et al, 1985, supra)
h = subtilisin 309 (International Patent Application No. PCT/DK 88/00002)
i = subtilisin 147 (International Patent Application No. PCT/DK 88/00002)
j = thermitase (Meloun et al, 1985, supra)
k = proteinase K (Betzel et al, 1988, Eur. J. Biochem. 178:155 ff and Gunkel et al, 1989, Eur. J. Biochem. 179:185 ff)
l = agualysin (Kwon et al, 1988, Eur. J. Biochem. 173:491 ff)
m = Bacillus PB92 protease (European Patent Publication No. 0 283 075)

TABLE I-continued

COMPARISON OF AMINO ACID SEQUENCE FOR
VARIOUS PROTEASES n = Protease TW7 (*Tritirachium album*) (International Patent Application No. PCT/US88/01040)
o = Protease TW3 (*Tritirachium album*) (International Patent Application No. PCT/US88/01040)
* = assigned deletion

```
No:              1                   10
a)   *-*-*-*-*-*-*-*-A-Q-S-*-V-P-Y-G-V-S-Q-I-K-*-*-*-*-*-A-P-A- b)   *-*-*-*-*-*-*-*-A-Q-S-*-V-P-Y-G-V-S-Q-I-K-*-*-*-*-*-A-P-A- c)   *-*-*-*-*-*-*-*-A-Q-S-*-V-P-Y-G-V-S-Q-I-K-*-*-*-*-*-A-P-A- d)   *-*-*-*-*-*-*-*-A-Q-S-*-V-P-Y-G-V-S-Q-I-K-*-*-*-*-*-A-P-A- e)   *-*-*-*-*-*-*-*-A-Q-T-*-V-P-Y-G-I-P-L-I-K-*-*-*-*-*-A-D-K- f)   *-*-*-*-*-*-*-*-A-Q-T-*-V-P-Y-G-I-P-L-I-K-*-*-*-*-*-A-D-K- g)   *-*-*-*-*-*-*-*-A-Q-T-*-V-P-Y-G-I-P-L-I-K-*-*-*-*-*-A-D-K- h)   *-*-*-*-*-*-*-*-A-Q-T-*-V-P-W-G-I-S-R-V-Q-*-*-*-*-*-A-P-A- i)   *-*-*-*-*-*-*-*-*-Q-T-*-V-P-W-G-I-S-F-I-N-*-*-*-*-*-T-Q-Q- j)   Y-T-P-N-D-P-Y-F-S-S-*-R-Q-Y-G-P-Q-K-I-Q-*-*-*-*-*-A-P-Q- k)   *-*-*-*-*-*-A-A-Q-T-N-A-P-W-G-L-A-R-I-S-S-T-S-P-G-T-S-T- l)   *-*-*-*-*-*-A-T-Q-S-P-A-P-W-G-L-D-R-I-D-Q-R-D-L-P-L-S-N- m)   *-*-*-*-*-*-*-*-A-Q-S-*-V-P-W-G-I-S-R-V-Q-*-*-*-*-*-A-P-A- n)   *-*-*-*-*-*-*-*-A-T-Q-E-D-A-P-W-G-L-A-R-I-S-S-Q-E-P-G-G-T-T- o)   *-*-*-*-*-*-*-*-A-E-Q-R-N-A-P-W-G-L-A-R-I-S-S-T-S-P-G-T-S-T-

No:             20                  30                  40
a)   L-H-S-Q-G-Y-T-G-S-N-V-K-V-A-V-I-D-S-G-I-D-S-S-H-P-D-L-*- b)   L-H-S-Q-G-Y-T-G-S-N-V-K-V-A-V-I-D-S-G-I-D-S-S-H-P-D-L-*- c)   L-H-S-Q-G-Y-T-G-S-N-V-K-V-A-V-I-D-S-G-I-D-S-S-H-P-D-L-*- d)   L-H-S-Q-G-Y-T-G-S-N-V-K-V-A-V-I-D-S-G-I-D-S-S-H-P-D-L-*- e)   V-Q-A-Q-G-Y-K-G-A-N-V-K-V-G-I-I-D-T-G-I-A-A-S-H-T-D-L-*- f)   V-Q-A-Q-G-F-K-G-A-N-V-K-V-A-V-L-D-T-G-I-Q-A-S-H-P-D-L-*- g)   V-Q-A-Q-G-F-K-G-A-N-V-K-V-A-V-L-D-T-G-I-Q-A-S-H-P-D-L-*- h)   A-H-N-R-G-L-T-G-S-G-V-K-V-A-V-L-D-T-G-I-*-S-T-H-P-D-L-*- i)   A-H-N-R-G-I-F-G-N-G-A-R-V-A-V-L-D-T-G-I-*-A-S-H-P-D-L-*- j)   A-W-*-D-I-A-E-G-S-G-A-K-I-A-I-V-D-T-G-V-Q-S-N-H-P-D-L-A- k)   Y-Y-Y-D-E-S-A-G-Q-G-S-C-V-Y-V-I-D-T-G-I-E-A-S-H-P-E-F-*- l)   S-Y-T-Y-T-A-T-G-R-G-V-N-V-Y-V-I-D-T-G-I-R-T-T-H-R-E-F-*- m)   A-H-N-R-G-L-T-G-S-G-V-K-V-A-V-L-D-T-G-I-*-S-T-H-P-D-L-*- n)   Y-R-Y-D-D-S-A-G-T-G-T-C-A-Y-I-I-D-T-G-I-Y-T-N-H-T-D-F-*- o)   Y-R-Y-D-D-S-A-G-Q-G-T-C-V-Y-V-I-D-T-G-V-E-A-S-H-P-E-F-*-

No:             50                  60
a)   *-K-V-A-G-G-A-S-M-V-P-S-E-T-N-P-F-*-*-Q-D-N-N-S-H-G-T-H-V-
```

-continued

```
b)   *-N-V-R-G-G-A-S-F-V-P-S-E-T-N-P-Y-*-*-Q-D-G-S-S-H-G-T-H-V- c)   *-N-V-R-G-G-A-S-F-V-P-S-E-T-N-P-Y-*-*-Q-D-G-S-S-H-G-T-H-V- d)   *-N-V-R-G-G-A-S-F-V-P-S-E-T-N-P-Y-*-*-Q-D-G-S-S-H-G-T-H-V- e)   *-K-V-V-G-G-A-S-F-V-S-G-E-S-*-Y-N-*-*-T-D-G-N-G-H-G-T-H-V- f)   *-N-V-V-G-G-A-S-F-V-A-G-E-A-*-Y-N-*-*-T-D-G-N-G-H-G-T-H-V- g)   *-N-V-V-G-G-A-S-F-V-A-G-E-A-*-Y-N-*-*-T-D-G-N-G-H-G-T-H-V- h)   *-N-I-R-G-G-A-S-F-V-P-G-E-P-*-S-T-*-*-Q-D-G-N-G-H-G-T-H-V- i)   *-R-I-A-G-G-A-S-F-I-S-S-E-P-*-S-Y-*-*-H-D-N-G-H-G-T-H-V- j)   G-K-V-V-G-G-W-D-F-V-D-N-D-S-T-P-*-*-*-Q-N-G-N-G-H-G-T-H-C- k)   *-*-*-E-G-R-A-Q-M-V-K-T-Y-Y-Y-S-S-*-*-R-D-G-N-G-H-G-T-H-C- l)   *-*-*-G-G-R-A-R-V-G-Y-D-A-L-G-G-N-G-*-Q-D-C-N-G-H-G-T-H-V- m)   *-N-I-R-G-G-A-S-F-V-P-G-E-P-*-S-T-*-*-Q-D-G-N-G-H-G-T-H-V- n)   *-*-*-G-G-R-A-K-F-L-K-N-F-A-G-D-G-Q-D-T-D-G-N-G-H-G-T-H-V- o)   *-*-*-E-G-R-A-Q-M-V-K-T-Y-Y-A-S-S-*-*-R-D-G-N-G-H-G-T-H-C-

No:       70              80              90
a)   A-G-T-V-A-A-L-*-N-N-S-I-G-V-L-G-V-A-P-S-A-S-L-Y-A-V-K-V- b)   A-G-T-I-A-A-L-*-N-N-S-I-G-V-L-G-V-A-P-S-A-S-L-Y-A-V-K-V- c)   A-G-T-I-A-A-L-*-N-N-S-I-G-V-L-G-V-S-P-S-A-S-L-Y-A-V-K-V- d)   A-G-T-I-A-A-L-*-N-N-S-I-G-V-L-G-V-A-P-S-A-S-L-Y-A-V-K-V- e)   A-G-T-V-A-A-L-*-D-N-T-T-G-V-L-G-V-A-P-N-V-S-L-Y-A-I-K-V- f)   A-G-T-V-A-A-L-*-D-N-T-T-G-V-L-G-V-A-P-S-V-S-L-Y-A-V-K-V- g)   A-G-T-V-A-A-L-*-D-N-T-T-G-V-L-G-V-A-P-S-V-S-L-Y-A-V-K-V- h)   A-G-T-I-A-A-L-*-N-N-S-I-G-V-L-G-V-A-P-S-A-E-L-Y-A-V-K-V- i)   A-G-T-I-A-A-L-*-N-N-S-I-G-V-L-G-V-A-P-S-A-D-L-Y-A-V-K-V- j)   A-G-I-A-A-A-V-T-N-N-S-T-G-I-A-G-T-A-P-K-A-S-I-L-A-V-R-V- k)   A-G-T-V-G-S-*-R-*-*-*-*-*-*-T-Y-G-V-A-K-K-T-Q-L-F-G-V-K-V- l)   A-G-T-I-G-G-V-*-*-*-*-*-*-*-T-Y-G-V-A-K-A-V-N-L-Y-A-V-R-V- m)   A-G-T-I-A-A-L-*-N-N-S-I-G-V-L-G-V-A-P-N-A-E-L-Y-A-V-K-V- n)   A-G-T-V-G-G-T-*-*-*-*-*-*-*-T-Y-G-V-A-K-K-T-S-L-F-A-V-K-V- o)   A-G-T-I-G-S-*-R-*-*-*-*-*-*-T-Y-G-V-A-K-K-T-Q-I-F-G-V-K-V-

No:       100             110             120
a)   L-G-A-D-G-S-G-Q-Y-S-W-I-I-N-G-I-E-W-*-A-I-A-*-N-N-M-D-*- b)   L-D-S-T-G-S-G-Q-Y-S-W-I-I-N-G-I-E-W-*-A-I-A-*-N-N-M-D-*- c)   L-D-S-T-G-S-G-Q-Y-S-W-I-I-N-G-I-E-W-*-A-I-A-*-N-N-M-D-*- d)   L-D-S-T-G-S-G-Q-Y-S-W-I-I-N-G-I-E-W-*-A-I-A-*-N-N-M-D-*- e)   L-N-S-S-G-S-G-T-Y-S-A-I-V-S-G-I-E-W-*-A-T-Q-*-N-G-L-D-*- f)   L-N-S-S-G-S-G-S-Y-S-G-I-V-S-G-I-E-W-*-A-T-T-*-N-G-M-D-*- g)   L-N-S-S-G-S-G-T-Y-S-G-I-V-S-G-I-E-W-*-A-T-T-*-N-G-M-D-*- h)   L-G-A-S-G-S-G-S-V-S-S-I-A-Q-G-L-E-W-*-A-G-N-*-N-G-M-H-*- i)   L-D-R-N-G-S-G-S-L-A-S-V-A-Q-G-I-E-W-*-A-I-N-*-N-N-M-H-*-
```

-continued

```
j)  L-D-N-S-G-S-G-T-W-T-A-V-A-N-G-I-T-Y-*-A-A-D-*-Q-G-A-K-*-
k)  L-D-D-N-G-S-G-Q-Y-S-T-I-I-A-G-M-D-F-V-A-S-D-K-N-N-R-N-C-
l)  L-D-C-N-G-S-G-S-T-S-G-V-I-A-G-V-D-W-V-*-T-*-R-N-H-R-R-P-
m)  L-G-A-S-G-S-G-S-V-S-S-I-A-Q-G-L-E-W-*-A-G-N-*-N-G-M-H-*-
n)  L-D-A-N-G-Q-G-S-N-S-G-V-I-A-G-M-D-F-V-T-K-D-A-S-S-Q-N-C-
o)  L-N-D-Q-G-S-G-Q-Y-S-T-I-I-S-G-M-D-F-V-A-N-D-Y-R-N-R-N-C-

No:                   130            140
a)  *-*-*-*-V-I-N-M-S-L-G-G-P-S-G-S-A-A-L-K-A-A-V-D-K-A-V-A-
b)  *-*-*-*-V-I-N-M-S-L-G-G-P-S-G-S-T-A-L-K-T-V-V-D-K-A-V-S-
c)  *-*-*-*-V-I-N-M-S-L-G-G-P-T-G-S-T-A-L-K-T-V-V-D-K-A-V-S-
d)  *-*-*-*-V-I-N-M-S-L-G-G-P-T-G-S-T-A-L-K-T-V-V-D-K-A-V-S-
e)  *-*-*-*-V-I-N-M-S-L-G-G-P-S-G-S-T-A-L-K-Q-A-V-D-K-A-Y-A-
f)  *-*-*-*-V-I-N-M-S-L-G-G-A-S-G-S-T-A-M-K-Q-A-V-D-N-A-Y-A-
g)  *-*-*-*-V-I-N-M-S-L-G-G-P-S-G-S-T-A-M-K-Q-A-V-D-N-A-Y-A-
h)  *-*-*-*-V-A-N-L-S-L-G-S-P-S-P-S-A-T-L-E-Q-A-V-N-S-A-T-S-
i)  *-*-*-*-I-I-N-M-S-L-G-S-T-S-G-S-S-T-L-E-L-A-V-N-R-A-N-N-
j)  *-*-*-*-V-I-S-L-S-L-G-G-T-V-G-N-S-G-L-Q-Q-A-V-N-Y-A-W-N-
k)  P-K-G-V-V-A-S-L-S-L-G-G-G-Y-S-S-S-V-N-S-A-A-A-*-R-L-Q-S-
l)  A-*-*-*-V-A-N-M-S-L-G-G-G-V-*-S-T-A-L-D-N-A-V-K-N-S-I-A-
m)  *-*-*-*-V-A-N-L-S-L-G-S-P-S-P-S-A-T-L-E-Q-A-V-N-S-A-T-S-
n)  P-K-G-V-V-V-N-M-S-L-G-G-P-S-S-S-A-V-N-R-A-A-A-*-E-I-T-S-
o)  P-N-G-V-V-A-S-M-S-I-G-G-G-Y-S-S-S-V-N-S-A-A-A-*-N-L-Q-Q-

No:         150            160            170
a)  S-G-V-V-V-A-A-A-G-N-E-G-T-S-G-S-S-S-T-V-G-Y-P-G-K-Y-P-
b)  S-G-I-V-V-A-A-A-A-G-N-E-G-S-S-G-S-S-S-T-V-G-Y-P-A-K-Y-P-
c)  S-G-I-V-V-A-A-A-A-G-N-E-G-S-S-G-S-T-S-T-V-G-Y-P-A-K-Y-P-
d)  S-G-I-V-V-A-A-A-A-G-N-E-G-S-S-G-S-T-S-T-V-G-Y-P-A-K-Y-P-
e)  S-G-I-V-V-V-A-A-A-G-N-S-G-S-S-G-S-Q-N-T-I-G-Y-P-A-K-Y-D-
f)  R-G-V-V-V-A-A-A-G-N-S-G-N-S-G-S-T-N-T-I-G-Y-P-A-K-Y-D-
g)  R-G-V-V-V-A-A-A-G-N-S-G-S-S-G-N-T-N-T-I-G-Y-P-A-K-Y-D-
h)  R-G-V-L-V-V-A-A-S-G-N-S-G-A-*-G-S-I-S-*-*-*-Y-P-A-R-Y-A-
i)  A-G-I-L-L-V-G-A-A-G-N-T-G-R-*-Q-G-V-N-*-*-*-Y-P-A-R-Y-S-
j)  K-G-S-V-V-A-A-A-G-N-A-G-N-T-A-P-N-*-*-*-*-Y-P-A-Y-Y-S-
k)  S-G-V-M-V-A-V-A-A-G-N-N-N-A-D-A-R-N-Y-S-*-*-*-P-A-S-E-P-
l)  A-G-V-V-Y-A-V-A-A-G-N-D-N-A-N-A-C-N-Y-S-*-*-*-P-A-R-V-A-
m)  R-G-V-L-V-V-A-A-S-G-N-S-G-A-*-G-S-I-S-*-*-*-Y-P-A-R-Y-A-
n)  A-G-L-F-L-A-V-A-A-G-N-E-A-T-D-A-S-S-S-S-*-*-*-P-A-S-E-E-
o)  S-G-V-M-V-A-V-A-A-G-N-N-N-A-D-A-R-N-Y-S-*-*-*-P-A-S-E-S-

No:              180            190            200
a)  S-V-I-A-V-G-A-V-D-S-S-N-Q-R-A-S-F-S-S-V-G-P-E-L-D-V-M-A-
b)  S-T-I-A-V-G-A-V-N-S-S-N-Q-R-A-S-F-S-S-A-G-S-E-L-D-V-M-A-
```

-continued

```
c)  S-T-I-A-V-G-A-V-N-S-S-N-Q-R-A-S-F-S-S-A-G-S-E-L-D-V-M-A-
d)  S-T-I-A-V-G-A-V-N-S-A-N-Q-R-A-S-F-S-S-A-G-S-E-L-D-V-M-A-
e)  S-V-I-A-V-G-A-V-D-S-N-K-N-R-A-S-F-S-S-V-G-A-E-L-E-V-M-A-
f)  S-V-I-A-V-G-A-V-D-S-N-S-N-R-A-S-F-S-S-V-G-A-E-L-E-V-M-A-
g)  S-V-I-A-V-G-A-V-D-S-N-S-N-R-A-S-F-S-S-V-G-A-E-L-E-V-M-A-
h)  N-A-M-A-V-G-A-T-D-Q-N-N-N-R-A-S-F-S-Q-Y-G-A-G-L-D-I-V-A-
i)  G-V-M-A-V-A-A-V-D-Q-N-G-Q-R-A-S-F-S-T-Y-G-P-E-I-E-I-S-A-
j)  N-A-I-A-V-A-S-T-D-Q-N-D-N-K-S-S-F-S-T-Y-G-S-V-V-D-V-A-A-
k)  S-V-C-T-V-G-A-S-D-R-Y-D-R-R-S-S-F-S-N-Y-G-S-V-L-D-I-F-G-
l)  E-A-L-T-V-G-A-T-T-S-S-D-A-R-A-S-F-S-N-Y-G-S-C-V-D-L-F-A-
m)  N-A-M-A-V-G-A-T-D-Q-N-N-N-R-A-S-F-S-Q-Y-G-A-G-L-D-I-V-A-
n)  S-A-C-T-V-G-A-T-D-K-T-D-T-L-A-E-Y-S-N-F-G-S-V-V-D-L-L-A-
o)  S-I-C-T-V-G-A-T-D-R-Y-D-R-R-S-S-F-S-N-Y-G-S-V-L-D-I-F-A-

No:              210               220
a)  P-G-V-S-I-Q-S-T-L-P-G-N-*-K-*-Y-G-A-Y-N-G-T-S-M-A-S-P-H-
b)  P-G-V-S-I-Q-S-T-L-P-G-G-*-T-*-Y-G-A-Y-N-G-T-S-M-A-T-P-H-
c)  P-G-V-S-I-Q-S-T-L-P-G-G-*-T-*-Y-G-A-Y-N-G-T-S-M-A-T-P-H-
d)  P-G-V-S-I-Q-S-T-L-P-G-G-*-T-*-Y-G-A-Y-N-G-T-S-M-A-T-P-H-
e)  P-G-V-S-V-Y-S-T-Y-P-S-N-*-T-*-Y-T-S-L-N-G-T-S-M-A-S-P-H-
f)  P-G-A-G-V-Y-S-T-Y-P-T-N-*-T-*-Y-A-T-L-N-G-T-S-M-A-S-P-H-
g)  P-G-A-G-V-Y-S-T-Y-P-T-S-*-T-*-Y-A-T-L-N-G-T-S-M-A-S-P-H-
h)  P-G-V-N-V-Q-S-T-Y-P-G-S-*-T-*-Y-A-S-L-N-G-T-S-M-A-T-P-H-
i)  P-G-V-N-V-N-S-T-Y-T-G-N-*-R-*-Y-V-S-L-S-G-T-S-M-A-T-P-H-
j)  P-G-S-W-I-Y-S-T-Y-P-T-S-*-T-*-Y-A-S-L-S-G-T-S-M-A-T-P-H-
k)  P-G-T-S-I-L-S-T-W-I-G-G-*-S-*-T-R-S-I-S-G-T-S-M-A-T-P-H-
l)  P-G-A-S-I-P-S-A-W-Y-T-S-D-T-A-T-Q-T-L-N-G-T-S-M-A-T-P-H-
m)  P-G-V-N-V-Q-S-T-Y-P-G-S-*-T-*-Y-A-S-L-N-G-T-S-M-A-T-P-H-
n)  P-G-T-D-I-K-S-T-W-N-D-G-R-T-K-I-I-S-*-*-G-T-S-M-A-S-P-H-
o)  P-G-T-D-I-L-S-T-W-I-G-G-S-T-R-S-I-S-*-*-G-T-S-M-A-T-P-H-

No:        230           240           250
a)  V-A-G-A-A-A-L-I-L-S-K-H-P-N-W-T-N-T-Q-V-R-S-S-L-E-N-T-T-
b)  V-A-G-A-A-A-L-I-L-S-K-H-P-T-W-T-N-A-Q-V-R-D-R-L-E-S-T-A-
c)  V-A-G-A-A-A-L-I-L-S-K-H-P-T-W-T-N-A-Q-V-R-D-R-L-E-S-T-A-
d)  V-A-G-A-A-A-L-I-L-S-K-H-P-T-W-T-N-A-Q-V-R-D-R-L-E-S-T-A-
e)  V-A-G-A-A-A-L-I-L-S-K-Y-P-T-L-S-A-S-Q-V-R-N-R-L-S-S-T-A-
f)  V-A-G-A-A-A-L-I-L-S-K-H-P-N-L-S-A-S-Q-V-R-N-R-L-S-S-T-A-
g)  V-A-G-A-A-A-L-I-L-S-K-H-P-N-L-S-A-S-Q-V-R-N-R-L-S-S-T-A-
h)  V-A-G-A-A-A-L-V-K-Q-K-N-P-S-W-S-N-V-Q-I-R-N-H-L-K-N-T-A-
i)  V-A-G-V-A-A-L-V-K-S-R-Y-P-S-Y-T-N-N-Q-I-R-Q-R-I-N-Q-T-A-
j)  V-A-G-V-A-G-L-L-A-S-Q-G-R-S-*-*-A-S-N-I-R-A-A-I-E-N-T-A-
k)  V-A-G-L-A-A-Y-L-M-T-L-G-K-T-T-A-A-S-A-C-R-*-Y-I-A-D-T-A-
```

```
-continued l)  V-A-G-V-A-A-L-Y-L-E-Q-N-P-S-A-T-P-A-S-V-A-S-A-I-L-N-G-A- m)  V-A-G-A-A-A-L-V-K-Q-K-N-P-S-W-S-N-V-Q-I-R-N-H-L-K-N-T-A- n)  V-A-G-L-G-A-Y-F-L-G-L-G-Q-K-V-Q-G-L-*-C-D-*-Y-M-V-E-K-G- o)  V-A-G-L-A-A-Y-L-M-T-L-G-R-A-T-A-S-N-A-C-R-*-Y-I-A-Q-T-A-

No:           260                 270       275
a)  T-K-L-G-D-S-F-Y-Y-*-G-K-G-L-I-N-V-Q-A-A-A-Q b)  T-Y-L-G-D-S-F-Y-Y-*-G-K-G-L-I-N-V-Q-A-A-A-Q c)  T-Y-L-G-N-S-F-Y-Y-*-G-K-G-L-I-N-V-Q-A-A-A-Q d)  T-Y-L-G-S-S-F-Y-Y-*-G-K-G-L-I-N-V-Q-A-A-A-Q e)  T-N-L-G-D-S-F-Y-Y-*-G-K-G-L-I-N-V-E-A-A-A-Q f)  T-Y-L-G-S-S-F-Y-Y-*-G-K-G-L-I-N-V-E-A-A-A-Q g)  T-Y-L-G-S-S-F-Y-Y-*-G-K-G-L-I-N-V-E-A-A-A-Q h)  T-S-L-G-S-T-N-L-Y-*-G-S-G-L-V-N-A-E-A-A-T-R i)  T-Y-L-G-S-P-S-L-Y-*-G-N-G-L-V-H-A-G-R-A-T-Q j)  D-K-I-S-G-T-G-T-Y-W-A-K-G-R-V-N-A-Y-K-A-V-Q-Y k)  N-K-G-D-L-S-N-I-P-F-G-T-V-N-L-L-A-Y-N-N-Y-Q-A l)  T-T-G-R-L-S-G-I-G-S-G-S-P-N-R-L-L-Y-S-L-L-S-S-G-S-G m)  T-S-L-G-S-T-N-L-Y-*-G-S-G-L-V-N-A-E-A-A-T-R n)  L-K-D-V-I-Q-S-V-P-S-D-T-A-N-V-L-I-N-N-G-E-G-S-A
```

SUMMARY OF THE INVENTION

Further investigations into these problems have now surprisingly shown that one of the critical factors in the use of subtilisin enzymes in detergent compositions is the adsorption of the enzyme to the substrate, i.e. the material to be removed from textiles, hard surfaces or other materials to be cleaned.

Consequently, the present invention relates to mutations of the subtilisin gene resulting in changed properties of the mutant subtilisin enzyme expressed by such a mutated gene, whereby said mutant subtilisin enzyme exhibits improved behavior in detergent compositions. Mutations are generated at specific nucleic acids in the parent subtilisin gene responsible for the expression of specific amino acids in specific positions in the subtilisin enzyme.

The present invention also relates to methods of selecting the positions and amino acids to be mutated and thereby mutatis mutandis the nucleic acids to be changed in the subtilisin gene in question.

The invention relates, in part, but is not limited to, mutations of the subtilisin 309 and subtilisin Carlsberg genes and ensuing mutant subtilisin 309 and Carlsberg enzymes, which exhibit improved wash performance in different detergent compositions resulting in wash liquors of varying pH values.

Furthermore, the invention relates to the use of the mutant enzymes in cleaning compositions and cleaning compositions comprising the mutant enzymes, especially detergent compositions comprising the mutant subtilisin enzymes.

It has surprisingly been found that a decrease in the isoelectric point and hence the net charge of a subtilisin-type protease under washing conditions, can result in not only an improved wash performance of the enzyme but also an improved compatibility with lipase.

It has also been surprisingly found that compatibility of protease with lipase is influenced not only by the pIo but by the positions at which the charges are located relative to the active site of the protease: the introduction of a negative charge or removal of a positive charge closer to the active site gives stronger improvement of compatibility of protease with lipase.

Accordingly, the invention provides in one aspect an enzymatic detergent composition comprising a lipase and a mutated subtilisin protease, wherein the net molecular electrostatic charge of the mutated protease has been changed by insertion, deletion or substitution of amino acid residues in comparison to the parent protease, and wherein, in said protease, there are, relative to said parent protease, fewer positively-charged amino acid residue(s) and/or more negatively-charged amino acid residue(s), whereby said subtilisin protease has an isoelectric pH lower than that of said parent protease.

BRIEF DESCRIPTION OF THE DRAWINGS

The invention is described further in detail in the following parts of this specification with reference to the drawings wherein.

DETAILED DESCRIPTION OF THE INVENTION

Figure 1:
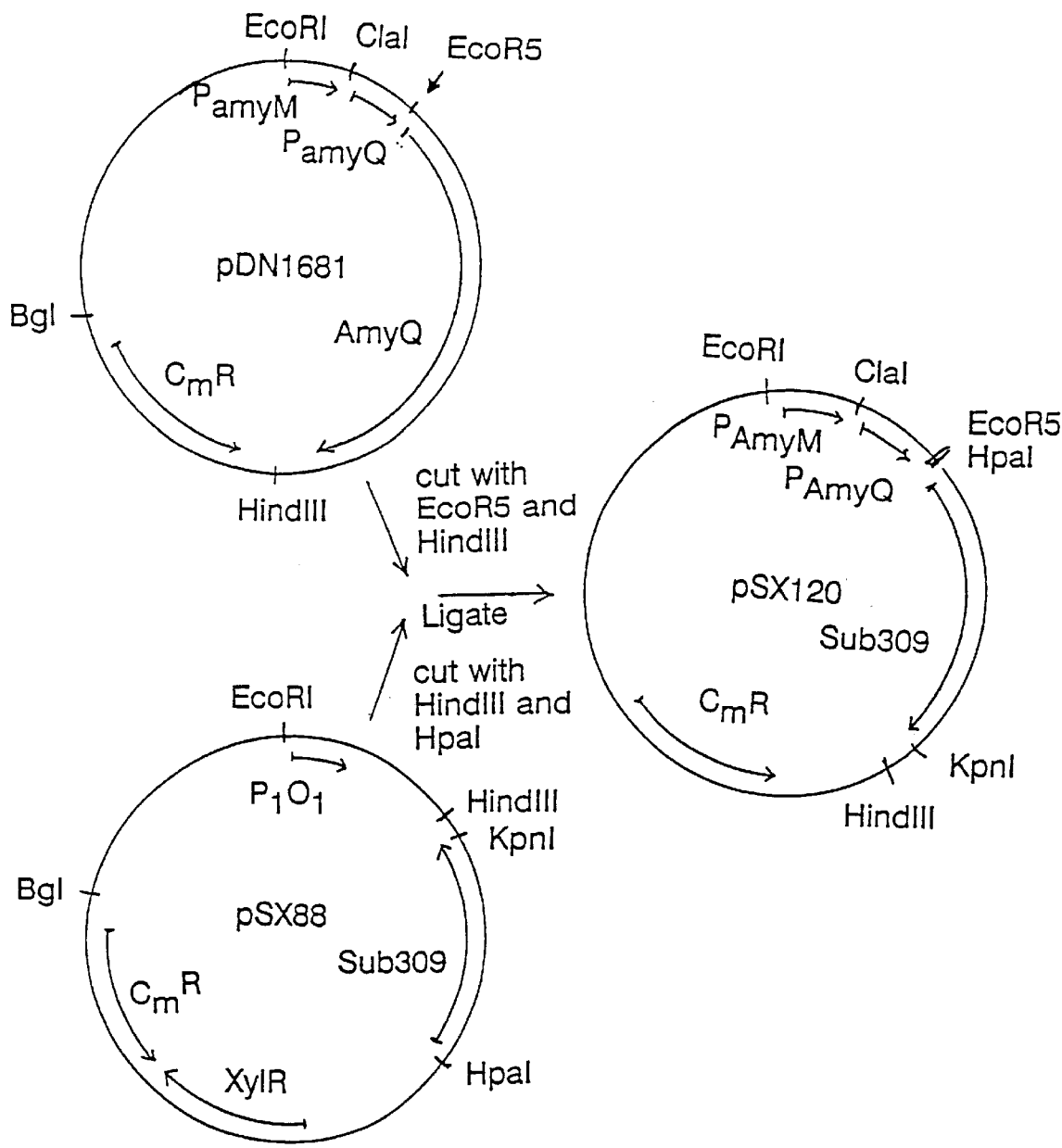
FIG. 1 shows the construction of plasmid pSX88.

As stated above, the present invention relates to mutated subtilisins in which the amino acid sequence has been changed through mutating the gene of the subtilisin enzyme, which it is desired to modify, in codons responsible for the expression of amino acids located on or close to the surface of the resulting enzyme.

In the context of this invention, a subtilisin is defined as a serine protease produced by gram-positive bacteria or fungi. In a more narrow sense, applicable to many embodiments of the invention, subtilisin also means a serine protease of gram-positive bacteria. According to another definition, a subtilisin is a serine protease, wherein the relative order of the amino acid residues in the catalytic triad is Asp—His—Ser (positions 32, 64 and 221). In a still more specific sense, many of the embodiments of the invention relate to serine proteases of gram-positive bacteria which can be brought into substantially unambiguous homology in their primary structure, with the subtilisins listed in Table I above.

Using the numbering system originating from the amino acid sequence of subtilisin BPN' provided in Table I above aligned with the amino acid sequence of a number of other known subtilisins, it is possible to indicate the position of an amino acid residue in a subtilisin enzyme unambiguously. Positions prior to amino acid residue number 1 in subtilisin BPN' are assigned a negative number, such as −6 for the N-terminal Y in thermitase, or 0 for the N-terminal A in proteinase K. Amino acid residues which are insertions in relation to subtilisin BPN' are numbered by the addition of letters in alphabetical order to the preceding subtilisin BPN' number, such as 12a, 12b, 12c, 12d, 12e for the "insert" S-T-S-P-G in proteinase K between $^{12}$Ser and $^{13}$Thr.

Using the above numbering system the positions of interest are:

1, 2, 3, 4, 6, 9, 10, 12, 14, 15, 17, 18, 19, 20, 21, 22, 24, 25, 27, 36, 37, 38, 40, 41, 43, 44, 45, 46, 49, 50, 51, 52, 53, 54, 55, 56, 57, 58, 59, 60, 61, 62, 75, 76, 77, 78, 79, 87, 89, 91, 94, 97, 98, 99, 100, 101, 103, 104, 105, 106, 107, 108, 109, 112, 113, 115, 116, 117, 118, 120, 126, 128, 129, 130, 131, 133, 134, 136, 137, 140, 141, 143, 144, 145, 146, 155, 156, 158, 159, 160, 161, 162, 163, 164, 165, 166, 167, 170, 171, 172, 173, 181, 182, 183, 184, 185, 186, 188, 189, 191, 192, 194, 195, 197, 204, 206, 209, 210, 211, 212, 213,. 214, 215, 216, 217, 218, 235, 236, 237, 238, 239, 240, 241, 242, 243, 244, 245, 247, 248, 249, 251, 252, 253, 254, 255, 256, 257, 259, 260, 261, 262, 263, 265, 269, 271, 272 and 275.

Isoelectric Point

Assuming that the substrate under washing conditions has an electrostatic charge opposite to that of the enzyme, it might be expected that the adsorption and thus the wash performance of the enzyme to the substrate would be improved by increasing the net electrostatic charge of the enzyme.

However, it was surprisingly found that a decrease in the NEC of the enzyme under such circumstances could result in an improved wash performance of the enzyme.

Stated differently, it was found that changing the isoelectric point of the enzyme in a direction to approach a lower pH, also shifted the pH of optimum wash performance of the enzyme to a lower value, meaning that in order to design an enzyme to a wash liquor of low pH, in which the enzyme is to be active, improvement in the wash performance of a known subtilisin enzyme may be obtained by mutating the gene for the known subtilisin enzyme to obtain a mutant enzyme having a lower $pI_o$.

This finding led to experiments showing that the opposite also is feasible. Meaning that a known subtilisin enzyme may also be designed for use in high pH detergents by shifting its $pI_o$ to higher values, thereby shifting the wash performance pH optimum for the enzyme to higher pH values.

The present invention therefore in one aspect relates to mutated subtilisin proteases, wherein the net electrostatic charge has been changed in comparison to the parent protease at the same pH, and which proteases have, relative to said parent protease, either fewer or more positively-charged amino acid residue(s) and/or more or fewer negatively-charged amino acid residue(s), or more or fewer positively-charged amino acid residue(s) and/or fewer or more negatively-charged amino acid residue(s) among the amino acid residues at any one or more of the following positions:

1, 2, 3, 4, 6, 9, 10, 12, 14, 15, 17, 18, 19, 20, 21, 22, 24, 25, 27, 36, 37, 38, 40, 41, 43, 44, 45, 46, 49, 50, 51, 52, 53, 54, 55, 56, 57, 58, 59, 60, 61, 62, 75, 76, 77, 78, 79,. 87, 89, 91, 94, 97, 98, 99, 100, 101, 103, 104, 105, 106, 107, 108, 109, 112, 113, 115, 116, 117, 118, 120, 126, 128, 129, 130, 131, 133, 134, 136, 137, 140, 141, 143, 144, 145, 146, 155, 156, 158, 159, 160, 161, 162, 163, 164, 165, 166, 167, 170, 171, 172, 173, 181, 182, 183, 184, 185, 186, 188, 189, 191, 192, 194, 195, 197, 204, 206, 209, 210, 211, 212, 213, 214, 215, 216, 217, 218, 235, 236, 237, 238, 239, 240, 241, 242, 243, 244, 245, 247, 248, 249, 251, 252, 253, 254, 255, 256, 257, 259, 260, 261, 262, 263, 265, 269, 271, 272 and 275 and whereby the isoelectric point of said subtilisin protease is lower or higher, respectively, than that of said parent protease.

In a preferred embodiment, the mutant subtilisin proteases of the present invention have, relative to said parent protease, either fewer or more positively-charged amino acid residue(s) and/or more or fewer negatively-charged amino acid residue(s), or either more or fewer positively-charged amino acid residue(s) and/or fewer or more negatively-charged amino acid residue(s), among the amino acid residues at any one or more of the following positions:

1, 2, 3, 4, 14, 15, 17, 18, 20, 27, 40, 41, 43, 44, 45, 46, 51, 52, 60, 61, 62, 75, 76, 78, 79, 91, 94, 97, 100, 105, 106, 108, 112, 113, 117, 118, 129, 130, 133, 134, 136, 137, 141, 143, 144, 145, 146, 165, 173, 181, 183, 184, 185, 191, 192, 206, 209, 210, 211, 212, 216, 239, 240, 242, 243, 244, 245, 247, 248, 249, 251, 252, 253, 255, 256, 257, 259, 263, 269, 271 and 272.

In another preferred embodiment, the mutant subtilisin proteases of the present invention have, relative to said parent protease, either fewer or more positively-charged amino acid residue(s) and/or more or fewer negatively-charged amino acid residue(s), or either more or fewer positively-charged amino acid residue(s) and/or fewer or more negatively-charged amino acid residue(s), among the amino acid residues at any one or more of positions:

1, 2, 3, 4, 14, 15, 17, 18, 20, 27, 40, 41, 43, 44, 45, 46, 51, 52, 60, 61, 62, 75, 76, 78, 79, 91, 94, 97, 100, 105, 106, 108, 112, 113, 117, 118, 129, 130, 133, 134, 136, 137, 141, 143, 144, 145, 146, 165, 173, 181, 183, 184, 185, 191, 192, 206, 209, 210, 211, 212, 216, 239, 240, 242, 243, 244, 245, 247, 248, 249, 251, 252, 253, 255, 256, 257, 259, 263, 269, 271 and 272 and at least one further mutation affecting an amino acid residue occupying one of the following positions:

1, 2, 3, 4, 6, 9, 10, 12, 14, 15, 17, 18, 19, 20, 21, 22, 24, 25, 27, 36, 37, 38, 40, 41, 43, 44, 45, 46, 49, 50, 51, 52, 53, 54, 55, 56, 57, 58, 59, 60, 61, 62, 75, 76, 77, 78, 79, 87, 89, 91, 94, 97, 98, 99, 100, 101, 103, 104, 105, 106, 107, 108, 109, 112, 113, 115, 116, 117, 118, 120, 126, 128, 129, 130, 131, 133, 134, 136, 137, 140, 141, 143, 144, 145, 146, 155, 156, 158, 159, 160, 161, 162, 163, 164, 165, 166, 167, 170, 171, 172, 173, 181, 182, 183, 184, 185, 186, 188, 189, 191, 192, 194, 195, 197, 204, 206, 209, 210, 211, 212, 213, 214, 215, 216, 217, 218, 235, 236, 237, 238, 239, 240, 241, 242, 243, 244, 245, 247, 248, 249, 251, 252, 253, 254, 255, 256, 257, 259, 260, 261, 262, 263, 265, 269, 271, 272 and 275.

In these aspects, the invention in short relates to mutant proteases in which the $pI_o$ of the mutant protease is lower than the $pI_o$ of the parent protease and the pH for optimum wash performance is also lower than the pH optimum for the parent protease; or mutant proteases wherein the $pI_o$ of the mutant protease is higher than the $pI_o$ of the parent protease and the pH for optimum wash performance is also higher than the pH optimum for the parent protease.

It is generally believed (Thomas, Russell and Fersht, supra) that kinetic properties can be influenced by changes in the electrostatic surface charge in the vicinity of the active site in the enzyme, but it has now surprisingly been found that changes in the kinetic properties of an enzyme can also be brought about by modifying surface charges remote from the active site.

Consequently, the invention is also considered to embrace mutant subtilisin enzymes, wherein one or more amino acid residues in a distance of more than 15 Å from the catalytic triad of said enzyme has been changed in comparison to the amino acid sequence of its parent enzyme, in a way to provide for a mutant protease having an isoelectric point shifted to achieve the pH for optimum wash performance of the enzyme, which pH optimum should be as close as possible to the pH of the wash liquor, wherein said mutant protease is intended for use.

In certain embodiments of the detergent compositions, the mutated subtilisin protease contains, relative to the corresponding parent protease, an amino acid residue within about 20 Å of the active site which has been changed by substitution, deletion, or adjacent insertion, e.g. at one or more of the following positions:

6, 27, 36–38, 44, 45, 49, 50–59, 61, 62, 89, 91, 98–101, 103–109, 112–3, 126–131, 136, 155, 156, 158–160, 162–164, 166, 167, 170, 171, 181, 182, 186, 188, 189, 195, 197, 204, 206, 209 and 211–218.

In certain further embodiments of the detergent compositions, the mutated subtilisin protease contains, relative to the corresponding parent protease, an amino acid residue at one or more the following positions which has been changed by substitution, insertion or deletion:

6, 9, 11, 12, 19, 25, 36, 37, 38, 53, 54, 55, 56, 57, 58, 59, 67, 71, 89, 111, 115, 120, 121, 122, 124, 128, 131, 140, 153, 154, 156, 158, 159, 160, 161, 162, 163, 164, 165, 166, 168, 170, 172, 175, 180, 182, 186, 187, 191, 194, 195, 199, 218, 219, 226, 234, 235, 236, 237, 238, 241, 260, 261, 262, 265, 268 and 275.

In further embodiments, the protease mutation can consist of an insertion of one or more amino acid residues at any of positions 36, 56, 159 and 164–166.

For example, the mutant proteases may contain an insertion mutation at position 36, e.g. the insertion of a negatively-charged amino acid residue (e.g. D or E), a neutral polar residue (e.g. A, Q or N) or a positive amino acid residue (e.g. R or K).

This is particularly applicable for example to subtilisin proteases 309 and 147 and PB92 and any other sequence for which the homology indicates that it naturally has an amino acid residue missing at position 36 relative to the sequence of subtilisin BPN'.

Insertion mutants at position 36 can have further mutations, for example at one or more of positions 120, 170, 195, 235, 251 and/or 76.

Suitable mutations at position 76 are e.g. negatively charged residues such as N76D or N76E.

Mutations at position 36 (especially insertion of negative or polar neutral residue) and at position 76 (substitution by negatively-charged residue) can often have stabilizing effect on the mutant protease and can be used in combination. Mutations at for example one or more of positions 120, 170, 195, 235 and 251 have been found to be associated with increased enzyme activity. Even in cases where these latter mutations are associated individually with some loss of stability it can be acceptable and useful to combine them with mutations at one or both of positions 36 and 76.

Useful examples of such protease mutants include those having the following mutations:

| reference code | amino acid substitution(s) |
|---|---|
| S021) | *36D |
| S022) | *36D + R170Y + G195E + K251E |
| S023) | *36D + H120D + R170Y + G195E + K235L |
| S024) | *36D + H120D + R170Y + G195E + K235L + K251E |
| S025) | *36D + H120D + G195E + K235L |
| S235) | *36D + N76D and |
| S035) | *36D + N76D + H120D + G195E + K235L. |

Under some conditions, it can be advantageous to arrange a further mutation by inserting a positive charge elsewhere, e.g. a positively-charged residue at position 213, e.g. T213K, in a mutant protease having an insertion of a negatively-charged amino acid residue at position 36. This can increase the water solubility of the resulting mutant protease.

According to the invention, it is further preferred that the mutant subtilisin enzyme represents a mutation of a parent enzyme selected from subtilisin BPN', subtilisin amylosacchariticus, subtilisin 168, subtilisin mesentericopeptidase, subtilisin Carlsberg, subtilisin DY, subtilisin 309, subtilisin 147, thermitase, Bacillus PB92 protease and proteinase K, preferably subtilisin 309, subtilisin 147, subtilisin Carlsberg, aqualysin, Bacillus PB92 protease, Protease TW7 or Protease TW3.

Further preferred embodiments comprise subtilisin enzymes containing one or more of the following mutations:

R10F, R10L, R10F+R45A+E89S+E136Q+R145A+ D181N+R186P+E271Q, R10F+R19Q+E89S+E136Q+ R145A+D181N+E271Q+R275Q, Q12K, Q12R, Q12K+ P14D+T22K+N43R+Q59E+N76D+A98R+S99D+S156E+ A158R+A172D+N173K+T213R+N248D+T255E+S256K+ S259D+A272R, Q12R+P14D+T22R+N43R+Q59E+ N76D+A98R+S99D+S156E+A158R+A172D+N173K+ T213R+N248D+T255E+S256K+S259D+A272R, Q12K+ P14D+T22K+T38K+N43R+Q59E+N76D+A98R+S99D+ S156E+A158R+A172D+N173K+T213R+N248D+T255E+ S256K+S259D+A272R, Q12R+P14D+T22R+T38R+ N43R+Q59E+N76D+A98R+S99D+S156E+A158R+ A172D+N173K+T213R+N248D+T255E+S256K+S259D+ A272R, Q12K+P14D+T22K+T38K+N43R+Q59E+N76D+

A98R+S99D+H120D+N140D+S141R+S156E+A158R+ A172D+N173K+T213R+N248D+T255E+S256K+S259D+ A272R, Q12R+P14D+T22R+T38R+N43R+Q59E+N76D+ A98R+S99D+H120D+N140D+S141R+S156E+A158R+ A172D+N173K+T213R+N248D+T255E+S256K+S259D+ A272R, P14D, P14K, P14K+*36D, P14K+N218D, P14K+ P129D, A15K, A15R, R19Q, T22K, T22R, K27R, K27V, D32*, *36D, *36D+R170Y+G195E+K251E, *36D+ H120D+R170Y+G195E+K235L, *36D+H120D+R170Y+ G195E+K235L+K251E, *36D+H120D+G195E+K235L, T38K, T38R, D41E, N43R, N43K, R45A, E53R, E53K, E53G+K235L, E54G, E54Y, Q59E, Q59E+N76D+A98R+ S99D+S156E+A158R+A172D+N173K+T213R+N248D+ T255E+S256K+S259D+A272R, D60N, N76D, E89S, E89S+K251N, Y91F, K94R, G97D, G97D+H120K, A98K, A98R, S99D, S99D+N140K, E112T, H120K, H120D, H120D+K235L, H120D+G195E+K235L, H120D+R170Y+ G195E+K235L, H120D+R170Y+G195E+K235L+K251E, P129D, E136Q, E136K, E136R, E136Q+R10L, N140D, N140K, N140R, S141K, S141R, R145A, S156E, S156E+ A158R+A172D+N173K, S156E+A158R+A172D+N173K+ T213R, S156E+A158R+A172D+N173K+T213R+N248D+ T255E+S256K+S259D+A272R, A158R, A158K, Y167V, R170Y, R170Y+G195E, R170Y+K251E, R170Y+G195E+ K251E, R170Y+G195E+K235L, Y171E, Y171T, A172D, N173K, D181N, N184K, N184R, N185D, R186P, Y192V, Y192V,A, G195E, G195D, G195E+T213R, G195E+K251E, G195E+K235L, D197N, D197K, D197E, Q206D, Q206E, Y209L, T213R, T213K, Y214T, Y214S, N218D, N218S, K235L, K235R, K237R, W241Y,L, W241Y+H249R, W241L+H249R, N248D, H249R, K251R, K251E, K251N, T255E, S256R, S256K, S259L, S259D, Y263W, S265K, S265R, E271Q, E271G, E271G+K27V, E271Q,G, A272R, R275Q, D14K, D14K+D120K, D14K+D120K+D140K, D14K+D120K+D140K+D172K, K27D, K27D+D120K, E54T, E54Y, N97D, N97D+S98D, N97D+T213D, S98D, S98D+T213D, D120K, D140K, S156E, D172K, T213D and N218D.

Further specific preferred embodiments are mutated subtilisin proteases comprising one or more of the following mutations:

S001) G195E
S002) G195D
S003) R170Y
S004) R170Y+G195E
S005) K251E
S006) H120D
S008) H120D+G195E
S009) T71D
S010) T71D+G195E
S011) R170Y+K251E
S012) R170Y+G195E+K251E
S013) T71D+R170Y+K251E
S014) T71D+R170Y+G195E+K251E
S015) K235L
S016) H120D+K235L
S017) H120D+G195E+K235L
S018) G195E+K251E
S019) H120D+R170Y+G195E+K235L
S020) H120D+R170Y+G195E+K235L+K251E
S021) *36D
S022) *36D+R170Y+G195E+K251E
S023) *36D+H120D+R170Y+G195E+K235L
S024) *36D+H120D+R170Y+G195E+K235L+K251E
S025) *36D+H120D+G195E+K235L
S026) E136R
S027) E89S
S028) D181N
S029) E89S+E136R
S030) E89S+D181N
S031) D197N+E271Q
S032) D197N
S033) E271Q
S035) *36D+N76D+H120D+G195E+K235L
S041) G195F
S201) N76D
S202) N76D+G195E
S203) N76D+R170Y+G195E
S204) H120D+G195E+K235L+K251E
S223) Q59E+N76D+A98R+S99D+T213K+K235L+ N248D+T255E+S256K+S259D+A272R
S224) Q59E+N76D+A98R+S99D+H120D+N140D+ S141R+K235L+N248D+T255E+S256K+S259D+ A272R
S225) *36D+Q59E+N76D+A98R+S99D+R170Y+ S156E+A158R+A172D+N173R+K235L+N248D+ T255E+S256K+S259D+A272R
S226) *36Q
S227) *36D+Q59E+N76D+A98R+S99D+H120D+ N140D+S141R+R170Y+G195E+K235L+N248D+ T255E+S256K+S259D+A272R
S228) *36D+Q59E+N76D+A98R+S99D+H120D+ N140D+S141R+S156E+A158R+A172D+N173K+ K235L+N248D+T255E+S256K+S259D+A272R
S229) Q59E+N76D+A98R+S99D+H120D+N140D+ S141R+S156E+A158R+A172D+N173K+K235L+ N248D+T255E+S256K+S259D+A272R
S234) Q206D
S235) *36D+N76D
S242) *36Q+N76D+H120D+G195E+K235L
C001) D14K
C002) D120K
C003) D140K
C004) D14K+D120K
C005) K27D
C006) K27D+D120K
C008) D172K
C009) D14K+D120K+D140K
C010) D14K+D120K+D140K+D172K
C013) N97D
C014) S98D
C015) T213D
C017) S156E
C018) N97D+S98D
C019) N97D+T213D
C022) S98D+T213D
C028) N218D
C100) V51D
C101) E54T and
C102) E54Y.

The S series mutants preferably are based on subtilisin 309 as the parent subtilisin. The C series mutants preferably are based on subtilisin Carlsberg.

In a further aspect of the invention, the above observations about the $pI_o$ are further utilized in a method for determining or selecting the position(s) and the amino acid(s) to be deleted, substituted or inserted for the amino acid(s) in a parent enzyme, so that the net electrostatic charge of the mutant enzyme has been changed in comparison to the NEC of the parent enzyme calculated at the same pH value.

Another way of expressing this principle covered by the invention is that the position(s) and the amino acid(s) to be deleted, substituted or inserted for the amino acid(s) in said parent enzyme is selected in a way whereby the total number of charges or total charge content (=TCC) and/or the NEC in a resulting mutant enzyme is changed in a way to provide for a mutant protease having an isoelectric point shifted to achieve the pH for optimum wash performance of the enzyme, which pH optimum should be as close as possible to the pH of the wash liquor, wherein said mutant protease is intended for use.

As indicated above, the $pI_o$ of a macromolecule such as an enzyme is calculated as the pH where the NEC of the molecule is zero. The procedure is exemplified in the examples below, but the principles are described in more detail here.

pK values are assigned to each potentially charged amino acid residue. Then the ratio of the occurrence of an amino acid residue at a given pH in charged or uncharged form (charged/uncharged, C/U(i)) is calculated for both negative and positive charges by using formulas Ia and Ib:

$$C/U(i)=\exp(ln_{10}(pH-pK_i))\text{(negative charge)} \quad \text{(Ia)}$$

$$C/U(i)=\exp(ln_{10}(pK_i-pH))\text{(positive charge)} \quad \text{(Ib)}.$$

According to the above formulas, if pH equals $pK_i$, $C/U(i)$ is equal to 1.

The relative charge, $Q_r(i)$, or charge contribution allocated to each charged residue is then calculated by using formulas IIa and IIb:

$$Q_r(i)=C/U(i)/(1+C/U(i))\text{(negative charge)} \quad \text{(IIa)}$$

$$Q_r(i)=-C/U(i)/(1+C/U(i))\text{(positive charge)} \quad \text{(IIb)}.$$

The pH value where the sum of all the charge contributions from the charged residues is equal to zero is found by iteration or through interpolation in a sufficiently dense pH-charge sum table.

Detergent Compositions Comprising the Mutant Enzymes

The present invention is also directed to the use of the mutant enzymes of the invention in cleaning and detergent compositions and to compositions comprising the mutant subtilisin enzymes.

Such compositions comprise one or more of the mutant subtilisin enzymes according to the present invention alone or in combination with a lipase or any of the usual components included in such compositions which are well-known to the person skilled in the art.

Such components include builders, such as phosphate or zeolite builders, surfactants such as anionic, cationic or non-ionic, polymers such as acrylic or equivalent polymers, bleach systems such as perborate- or amino-containing bleach precursors or activators, structurants such as silicate structurants, alkali or acid to adjust pH, humectants and/or neutral inorganic salts.

In several useful embodiments the detergent compositions can be formulated as follows:

a) A detergent composition formulated as a detergent powder containing phosphate builder, anionic surfactant, nonionic surfactant, acrylic or equivalent polymer, perborate bleach precursor, amino-containing bleach activator, silicate or other structurant, alkali to adjust to desired pH in use and neutral inorganic salt.

b) A detergent composition formulated as a detergent powder containing zeolite builder, anionic surfactant, nonionic surfactant, acrylic or equivalent polymer, perborate bleach precursor, amino-containing bleach activator, silicate or other structurant, alkali to adjust to desired pH in use and neutral inorganic salt.

c) A detergent composition formulated as an aqueous detergent liquid comprising anionic surfactant, nonionic surfactant, humectant, organic acid, caustic alkali, with a pH adjusted to a value between 9 and 10.

d) A detergent composition formulated as a nonaqueous detergent liquid comprising a liquid nonionic surfactant consisting essentially of linear alkoxylated primary alcohol, triacetin, sodium triphosphate, caustic alkali, perborate monohydrate bleach precursor and tertiary amine bleach activator, with a pH adjusted to a value between about 9 and 10.

e) A detergent composition formulated as a detergent powder in the form of a granulate having a bulk density of at least 550 g/l, e.g. at least 600 g/l, containing anionic and nonionic surfactants, e.g. anionic surfactant and a mixture of nonionic surfactants with respective alkoxylation degrees about 7 and about 3, low or substantially zero neutral inorganic salt, phosphate builder, perborate bleach precursor, tertiary amine bleach activator, sodium silicate and minors and moisture.

f) A detergent composition formulated as a detergent powder in the form of a granulate having a bulk density of at least 600 g/l, containing anionic surfactant and a mixture of nonionic surfactants with respective alkoxylation degrees about 7 and about 3, low or substantially zero neutral inorganic salt, zeolite builder, perborate bleach precursor, tertiary amine bleach activator, sodium silicate and minors and moisture.

g) A detergent composition formulated as a detergent powder containing anionic surfactant, nonionic surfactant, acrylic polymer, fatty acid soap, sodium carbonate, sodium sulphate, clay particles with or without amines, perborate bleach precursor, tertiary amine bleach activator, sodium silicate and minors and moisture.

h) A detergent composition formulated as a detergent (soap) bar containing soap based on pan-saponified mixture of tallow and coconut oil, neutralized with orthophosphoric acid, mixed with protease, also mixed with sodium formate, borax, propylene glycol and sodium sulphate, and then plodded on a soap production line.

i) An enzymatic detergent composition formulated to give a wash liquor pH of 9 or less when used at a rate corresponding to 0.4–0.8 g/l surfactant.

j) An enzymatic detergent composition formulated to give a wash liquor pH of 8.5 or more when used at a rate corresponding to 0.4–0.8 g/l surfactant.

k) An enzymatic detergent composition formulated to give a wash liquor ionic strength of 0.03 or less, e.g. 0.02 or less, when used at a rate corresponding to 0.4–0.8 g/l surfactant.

l) An enzymatic detergent composition formulated to give a wash liquor ionic strength of 0.01 or more, e.g. 0.02 or more, when used at a rate corresponding to 0.4–0.8 g/l surfactant.

m) A structured liquid detergent containing e.g. 2–15% nonionic surfactant, 5–40% total surfactant comprising nonionic and optionally anionic surfactant, 5–35% phosphate-containing or non-phosphate-containing builder, 0.2–0.8% polymeric thickener, e.g. crosslinked acrylic polymer with m.w. over $10^6$, at least 10% sodium silicate, e.g. as neutral waterglass, alkali (e.g. potassium-containing alkali) to adjust to desired pH, preferably in the range 9–10 or upwards, e.g. above pH 11, with a ratio of sodium cation:silicate anion (as free silica) (by weight) of less than 0.7:1, and viscosity of 0.3–30 Pa.s (at 20° C. and 20 reciproval secs).

For example, such detergents can contain about 5% nonionic surfactant C13–15 alcohol alkoxylated with about 5 EO groups per mole and about 2.7 PO groups per mole, 15–23% neutral waterglass with 3.5 weight ratio between silica and sodium oxide, 13–19% KOH, 8–23% STPP, 0–11% sodium carbonate, 0.5% Carbopol 941™. Protease may be incorporated at for example 0.5% of example S1.

The protease can be used in an amount ranging from e.g. about 0.0002 to about 0.05 Anson units per gram of the detergent composition. Expressed in other units, the protease can also be included in the compositions in amounts of the order of from about 1 to about 100 GU/mg detergent formulation. Preferably, the amount ranges from 2 to 50 and particularly preferably from 5 to 20 GU/mg.

A GU is a Glycine Unit and is defined as the proteolytic enzyme activity which produces an amount of $NH_2$-group equivalent to 1 micromole of glycine during a 15-minute-incubation at 40° C. with N-acetyl casein as substrate under standard conditions.

Detergent Compositions Comprising Mutant Enzymes and Lipases

It has surprisingly been found that a decrease in the isoelectric point and hence net charge of a subtilisin type protease under washing conditions, can result in not only an improved wash performance of the enzyme but also an improved compatibility with lipase.

It also has been surprisingly found that compatibility of protease with lipase is influenced not only by the $pI_o$ but also by the positions at which the charges are located relative to the active site of the protease. The introduction of negative charge or removal of positive charge closer to the active site gives stronger improvement of compatibility of protease with lipase.

Accordingly, certain embodiments of the invention provide enzymatic detergent compositions comprising lipase and mutated subtilisin protease, wherein the net molecular electrostatic charge of the mutated protease has been changed by insertion, deletion or substitution of amino acid residues in comparison to the parent protease and wherein, there are, relative to said parent protease, fewer positively-charged amino acid residue(s) and/or more negatively-charged amino acid residue(s), whereby said subtilisin protease has an isoelectric point lower than that of said parent protease.

One preferred class of lipases for such use originates in Gram-negative bacteria and includes e.g. lipase enzymes of the groups defined in EP 0 205 208 and 0 206 390 (both to Unilever), (hereby incorporated by reference), including lipases immunologically related to those from certain *Ps. fluorescens, P. gladioli* and Chromobacter strains.

Preferred embodiments of mutantations of the subtilisin protease enzyme for use in conjunction with lipase include one or more mutations at the site of an amino acid residue located within the range of about 15A–20A from the active site, especially for example at positions 170, 120 or 195.

The lipase can usefully be added in the form of a granular composition (alternatively a solution or a slurry) of lipolytic enzyme with carrier material (e.g. as in EP 258068 (Novo Nordisk A/S) and Savinase® and Lipolase®, products of Novo Nordisk A/S).

The added amount of lipase can be chosen within wide limits, for example 50 to 30,000 LU/g per gram of the surfactant system or of the detergent composition, e.g. often at least 100 LU/g, very usefully at least 500 LU/g, sometimes preferably above 1000, above 2000 LU/g or above 4000 LU/g or more, thus very often within the range 50–4000 LU/g and possibly within the range 200–1000 LU/g. In this specification lipase units are defined in EP 258068.

The lipolytic enzyme can be chosen from among a wide range of lipases, e.g. the lipases described in the following patent specifications, EP 214761 (Novo Nordisk A/S), EP 0 258 068. Further preferred lipases include lipases showing immunological cross-reactivity with antisera raised against lipase from *Thermomyces lanuginosus* ATCC 22070, EP 0 205 208 and EP 0 206 390 and lipases showing immunological cross-reactivity with antisera raised against lipase from *Chromobacter viscosum var lipolyticum* NRRL B-3673, or against lipase from Alcaligenes PL-679, ATCC 31371 and FERM-P 3783. Also preferred are the lipases described in specifications WO 87/00859 (Gist-Brocades) and EP 0 204 284 (Sapporo Breweries). Suitable in particular are for example the following commercially available lipase preparations: Novo Lipolase®, Amano lipases CE, P, B, AP, M-AP, AML and CES, and Meito lipases MY-30, OF and PL, also Esterase® MM, Lipozym®, SP225, SP285, Saiken lipase, Enzeco lipase, Toyo Jozo lipase and Diosynth lipase (Trademarks).

Genetic engineering of the enzymes can be achieved by extraction of an appropriate lipase gene, e.g. the gene for lipase from Thermomyces lanuginosus or from a mutant thereof, and introduction and expression of the gene or derivative thereof in a suitable producer organism such as an Aspergillus. The techniques described in WO 88/02775 (Novo Nordisk A/S), EP 0 243 338 (Labofina), EP 0 268 452 (Genencor) and notably EP 0 305 216 (Novo Nordisk A/S) or EP 0 283 075 (Gist-Brocades) may be applied and adapted.

Similar considerations apply mutatis mutandis in the case of other enzymes, which may also be present. Without limitation: Amylase can for example be used when present in an amount in the range about 1 to about 100 MU (maltose units) per gram of detergent composition, (or 0.014–1.4, e.g. 0.07–0.7, KNU/g (Novo units)). Cellulase can for example be used when present in an amount in the range about 0.3 to about 35 CEVU units per gram of the detergent composition.

The detergent compositions may furthermore include the following usual detergent ingredients in the usual amounts. They may be built or unbuilt and may be of the zero-P type (i.e. not containing any phosphorus-containing builders). Thus, the composition may contain in aggregate for example from 1–50%, e.g. at least about 5% and often up to about 35–40% by weight, of one or more organic and/or inorganic builders. Typical examples of such builders include those already mentioned above and more broadly include alkali metal ortho, pyro and tripolyphosphates, alkali metal carbonates, either alone or in admixture with calcite, alkali metal citrates, alkali metal nitrilotriacetates, carboxymethyloxysuccinates, zeolites, polyacetalcarboxylates and so on.

Furthermore, the detergent compositions may contain from 1–35% of a bleaching agent or a bleach precursor or a system comprising bleaching agent and/or precursor with activator therefor. Further optional ingredients are lather boosters, foam depressors, anti-corrosion agents, soil-suspending agents, sequestering agents, anti-soil redeposition agents, perfumes, dyes, stabilizing agents for the enzymes and so on.

The compositions can be used for the washing of textile materials, especially but without limitation cotton and polyester-based textiles and mixtures thereof. Especially suitable are for example washing processes carried out at temperatures of about 60–65° C. or lower, e.g. about 30° C.–35° C. or lower. It can be very suitable to use the compositions at a rate sufficient to provide about e.g. 0.4–0.8 g/l surfactant in the wash liquor, although it is of course possible to use lesser or greater concentrations if desired. Without limitation it can be stated that a use-rate e.g. from about 3 g/l to about 6 g/l of the detergent formulation is suitable when the formulations provided in the Examples are used.

Method for Producing Mutations in Subtilisin Genes

Many methods for introducing mutations into genes are well known in the art. After a brief discussion of cloning subtilisin genes, methods for generating mutations in both random sites and specific sites within the subtilisin gene will be discussed.

Cloning a Subtilisin Gene

The gene encoding subtilisin may be cloned from any Gram-positive bacteria or fungus by various methods well known in the art. First a genomic and/or cDNA library of DNA must be constructed using chromosomal DNA or messenger RNA from the organism that produces the subtilisin to be studied. Then, if the amino acid sequence of the subtilisin is known, homologous, labelled oligonucleotide probes may be synthesized and used to identify subtilisin-encoding clones from a genomic library of bacterial DNA or from a fungal cDNA library. Alternatively, a labelled oligonucleotide probe containing sequences homologous to subtilisin from another strain of bacteria or fungus could be used as a probe to identify subtilisin-encoding clones, using hybridization and washing conditions of lower stringency.

Yet another method for identifying subtilisin-producing clones involves inserting fragments of genomic DNA into an expression vector, such as a plasmid, transforming protease-negative bacteria with the resulting genomic DNA library and then plating the transformed bacteria onto agar containing a substrate for subtilisin, such as skim milk. Those bacteria containing subtilisin-bearing plasmid will produce colonies surrounded by a halo of clear agar due to the digestion of skim milk by excreted subtilisin.

Generation of Random Mutations in the Subtilisin Gene

Once the subtilisin gene has been cloned into a suitable vector, such as a plasmid, several methods can be used to introduce random mutations into the gene.

One method would be to incorporate the cloned subtilisin gene as part of a retrievable vector into a mutator strain of *Eschericia coli*.

Another method would involve generating a single stranded form of the subtilisin gene and then annealing the fragment of DNA containing the subtilisin gene with another DNA fragment so that a portion of the subtilisin gene remained single stranded. This discrete, single stranded region could then be exposed to any of a number of mutagenizing agents, including, but not limited to, sodium bisulfite, hydroxylamine, nitrous acid, formic acid or hydralazine. A specific example of this method for generating random mutations is described by Shortle and Nathans (1978, Proc. Natl. Acad. Sci. U.S.A., 75: 2170–2174). According to this method, the plasmid bearing the subtilisin gene would be nicked by a restriction enzyme that cleaves within the gene. This nick would be widened into a gap using the exonuclease action of DNA polymerase I. The resulting single-stranded gap could then be mutagenized using any one of the above mentioned mutagenizing agents.

Alternatively, the subtilisin gene from a Bacillus species including the natural promoter and other control sequences could be cloned into a plasmid vector containing replicons for both *E. coli* and *B. subtilis*, a selectable phenotypic marker and the M13 origin of replication for production of single-stranded plasmid DNA upon superinfection with helper phage IR1. Single-stranded plasmid DNA containing the cloned subtilisin gene is isolated and annealed with a DNA fragment containing vector sequences but not the coding region of subtilisin, resulting in a gapped duplex molecule. Mutations are introduced into the subtilisin gene either with sodium bisulfite, nitrous acid or formic acid or by replication in a mutator strain of *E. coli* as described above. Since sodium bisulfite reacts exclusively with cytosine in a single-stranded DNA, the mutations created with this mutagen are restricted only to the coding regions. Reaction time and bisulfite concentration are varied in different experiments so that from one to five mutations are created per subtilisin gene on average. Incubation of 10 $\mu$g of gapped duplex DNA in 4 M Na-bisulfite, pH. 6.0, for 9 minutes at 37° C. in a reaction volume of 400 $\mu$l, deaminates about 1% of cytosines in the single-stranded region. The coding region of mature subtilisin contains about 200 cytosines, depending on the DNA strand. Advantageously, the reaction time is varied from about 4 minutes (to produce a mutation frequency of about one in 200) to about 20 minutes (about 5 in 200).

After mutagenesis, the gapped molecules are treated in vitro with DNA polymerase I (Klenow fragment) to make fully double-stranded molecules and fix the mutations. Competent *E. coli* are then transformed with the mutagenized DNA to produce an amplified library of mutant subtilisins. Amplified mutant libraries can also be made by growing the plasmid DNA in a Mut D strain of *E. coli* which increases the range for mutations due to its error prone DNA polymerase.

The mutagens nitrous acid and formic acid may also be used to produce mutant libraries. Because these chemicals are not as specific for single-stranded DNA as sodium bisulfite, the mutagenesis reactions are performed according to the following procedure. The coding portion of the subtilisin gene is cloned in M13 phage by standard methods and single stranded phage DNA is prepared. The single-stranded DNA is then reacted with 1 M nitrous acid pH. 4.3 for 15–60 minutes at 23° C. or 2.4 M formic acid for 1–5 minutes at 23° C. These ranges of reaction times produce a mutation frequency of from 1 in 1000 to 5 in 1000. After mutagenesis, a universal primer is annealed to the M13 DNA and duplex DNA is synthesized using the mutagenized single-stranded DNA as a template so that the coding portion of the subtilisin gene becomes fully double-stranded. At this point, the coding region can be cut out of the M13 vector with restriction enzymes and ligated into an unmutagenized expression vector so that mutations occur only in the restriction fragment (Myers et al., Science 229:242–257 (1985)).

Generation of Site Directed Mutations in the Subtilisin Gene

Once the subtilisin gene has been cloned and desirable sites for mutation identified, these mutations can be introduced using synthetic oligonucleotides. These oligonucleotides contain nucleotide sequences flanking the desired mutation sites; mutant nucleotides are inserted during oligonucleotide synthesis. In a preferred method, a single stranded gap of DNA bridging the subtilisin gene is created in a vector bearing the subtilisin gene. The synthetic nucleotide bearing the desired mutation is then annealed to a homologous portion of the single-stranded DNA. The remaining gap is then filled in by DNA polymerase I (Klenow fragment) and the construct is ligated using T4 ligase. A specific example of this method is described in Morinaga et al. (1984, Biotechnology 2:646–639). According to Morinaga et al., a fragment within the gene is removed using restriction endonuclease. The vector/gene, now containing a gap, is then denatured and hybridized to a vector/gene which, instead of containing a gap, has been cleaved with another restriction endonuclease at a site outside the area involved in the gap. A single-stranded region of the gene is then available for hybridization with mutated oligonucleotides, the remaining gap is filled in by the Klenow fragment of DNA polymerase I, the insertions are ligated with T4 DNA ligase and after one cycle of replication, a double-stranded plasmid bearing the desired mutation is produced. The Morinaga method obviates the additional manipulation of constructing new restriction sites and therefore facilitates the generation of mutations at multiple sites. U.S. Pat. No. 4,760,025 by Estell et al., issued Jul. 26, 1988, is able to introduce oligonucleotides bearing multiple mutations by performing minor alterations of the cassette. However, an even greater variety of mutations can be introduced at any one time by the Morinaga method, because a multitude of oligonucleotides of various lengths can be introduced.

Expression of Subtilisin Mutants

According to the present invention, a mutated subtilisin gene produced by the methods described above or any other method known in the art, can be expressed in enzyme form using an expression vector. An expression vector generally falls under the definition of a cloning vector, since an expression vector usually includes the components of a typical cloning vector, namely, an element that permits autonomous replication of the vector in a microorganism independent of the genome of the microorganism, and one or more phenotypic markers for selection purposes. An expression vector includes control sequences encoding a promoter, operator, ribosome binding site, translation initiation signal and, optionally, a repressor gene or various activator genes. To permit the secretion of the expressed protein, nucleotides encoding a "signal sequence" may be inserted prior to the coding sequence of the gene. For expression under the direction of control sequences, a target gene to be treated according to the invention is-operably linked to the control sequences in the proper reading frame. Promoter sequences that can be incorporated into plasmid vectors and which can support the transcription of the mutant subtilisin gene, include but are not limited to the prokaryotic β-lactamase promoter (Villa-Kamaroff et al., 1978, Proc. Natl. Acad. Sci. U.S.A. 75:3727–3731) and the tac promoter (DeBoer et al., 1983, Proc. Natl. Acad. Sci. U.S.A. 80:21–25). Further references can also be found in "Useful proteins from recombinant bacteria" in Scientific American, 1980, 242:74–94.

According to one embodiment B. subtilis is transformed by an expression vector carrying the mutated DNA. If expression is to take place in a secreting microorganism such as B. subtilis a signal sequence may follow the translation initiation signal and precede the DNA sequence of interest. The signal sequence acts to transport the expression product to the cell wall where it is cleaved from the product upon secretion. The term "control sequences" as defined above is intended to include a signal sequence, when it is present.

EXAMPLES

Site Specific Mutation of the Subtilisin Gene Generates Mutants With Useful Chemical Characteristics

MATERIALS AND METHODS

Bacterial Strains

B. subtilis 309 and 147 are variants of Bacillus lentus deposited with the NCIB and accorded accession numbers NCIB 10147 and NCIB 10309 and described in U.S. Pat. No. 3,723,250, issued Mar. 27, 1973, which is incorporated herein by reference.

B. subtilis DN 497 is described in U.S. Ser. No. 039,298 filed Apr. 17, 1987, corresponding to EP Publ. No. 242 220, which are also incorporated herein by reference, and is an aro+ transformant of RUB 200 with chromosomal DNA from SL 438, a sporulation and protease deficient strain obtained from Dr. Kim Hardy of Biogen.

E. coli MC 1000 $r^{-m}+$ (Casadaban, M. J. and Cohen, S. N. (1980), J. Mol. Biol. 138: 179–207), was made $r^{-m}+$ by conventional methods and is also described in U.S. Ser. No. 039,298.

B. subtilis DB105 is described in Kawamura, F., Doi, R. H. (1984), Construction of a Bacillus subtilis double mutant deficient in extracellular alkaline and neutral proteases, J. Bacteriol. 160 (2), 442–444.

Figure 3:
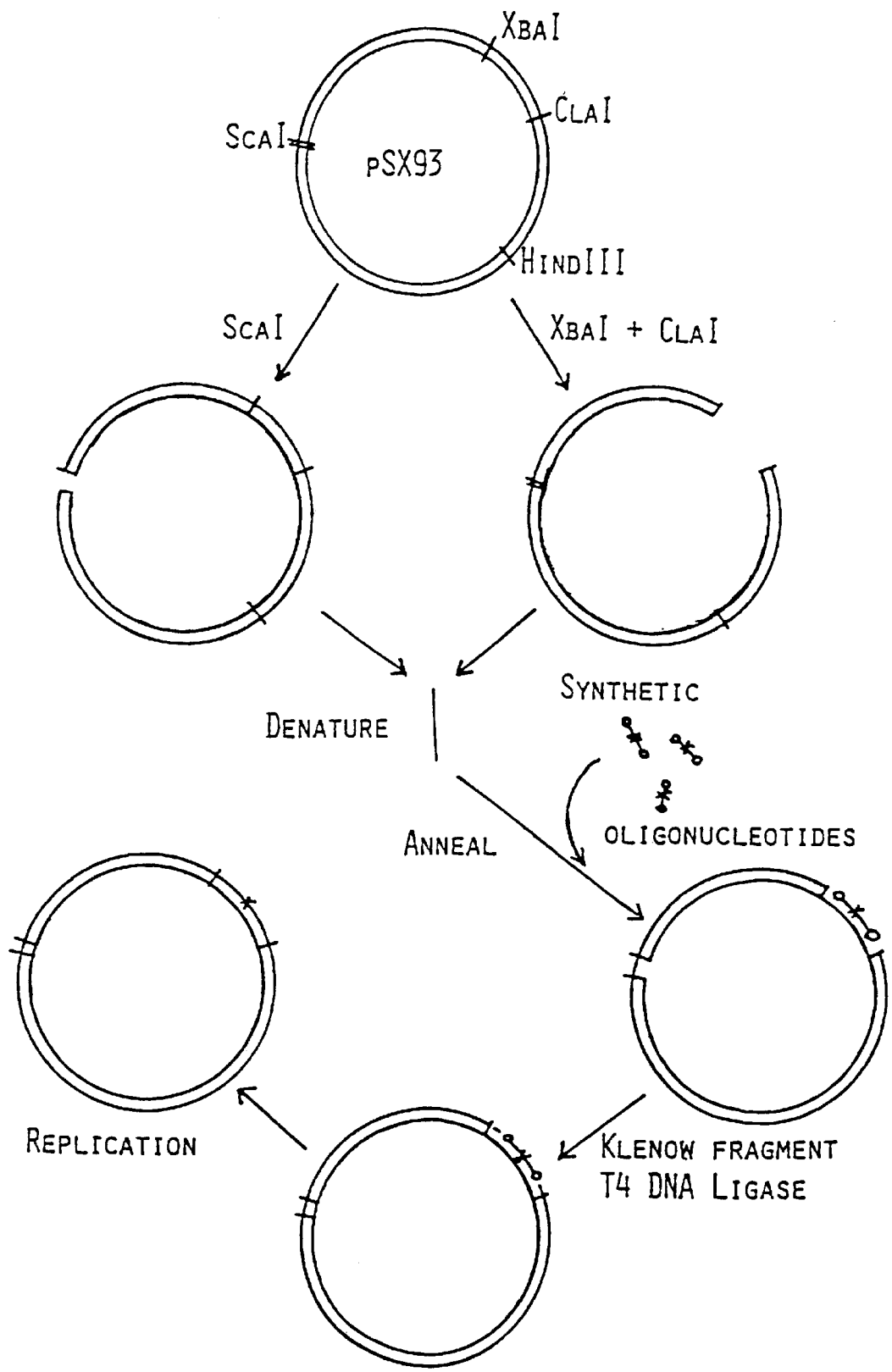
FIG. 3 exemplifies the construction of the mutant subtilisin 309 genes for expressing the enzymes of the invention.

Plasmids pSX50 (described in U.S. Ser. No. 039,298 which is incorporated herein by reference) is a derivative of plasmid pDN 1050 comprising the promoter-operator $P_1O_1$, the B. pumilus xyn B gene and the B. subtilis xyl R gene.

pSX62 (described in U.S. Ser. No. 039,298, supra) is a derivative of pSX52 (ibid), which comprises a fusion gene between the calf prochymosin gene and the B. pumilus xyn B gene inserted into pSX50 (supra). pSX62 was generated by inserting the E. coli rrn B terminator into pSX52 behind the prochymosin gene.

pSX65 (described in U.S. Ser. No. 039,298, supra) is a derivative of plasmid pDN 1050, comprising the promotor-operator $P_2O_2$ the B. pumilus xyn B gene and the B. subtilis xyl R gene.

pSX88 (described in unpublished International Patent Application No. PCT/DK 88/00002 (NOVO INDUSTRI A/S) which is incorporated herein by reference) is a derivative of pSX50 comprising the subtilisin 309 gene.

pSX92 was produced by cloning the subtilisin 309 into plasmid pSX62 (supra) cut at Cla I and Hind III and Cla I filled prior to the insertion of the fragments DraI-NheI and NheI-Hind III from the cloned subtilisin 309 gene.

pSX93, shown in FIG. 3, is pUC13 (Vieira and Messing, 1982, Gene 19::259–268) comprising a 0.7kb XbaI-Hind III fragment of the subtilisin 309 gene including the terminator inserted in a polylinker sequence.

pSX119 (described in unpublished International Patent Application No. PCT/DK 88/00002, supra) is pUC13 harboring an EcoRI-XbaI fragment of the subtilisin 309 gene inserted into the polylinker.

pSX120 is a plasmid where the HpaI-HindIII fragment with the subtilisin 309 gene from pSX88 is inserted into EcoRV-HindIII on pDN 1681, in a way whereby the protease gene is expressed by the amy M and amy Q promotors. pDN 1681 is obtained from pDN 1380 (Diderichsen, B. and Christiansen, L.: 1988, FEMS Microbiology Letters 56: 53–60) with an inserted 2.85 bp ClaI fragment from *B. amylolicuefaciens* carrying the amy Q gene with promotor (Takkinen et al.: 1983, J. Biol. Chem. 258: 1007ff).

pUC13 is described in Vieira, J. and Messing, J.: 1982, Gene 19: 259–268.

pUC19 is described in Yanisch-Perron, C., Vieira, J. and Messing, J., 1985, Gene 33:103–119.

pUB110 is described in Lacey, R. W., Chopra, J. (1974), Genetic studies of a multiresistant strain of *Staphylococcus aureus*, J. Med. Microbiol. 7, 285–297 and in Zyprian, E. and Matzura, H. (1986), Characterization of signals promoting gene expression on the *Staphylococcus aureus* plasmid pUB110 and development of a Gram-positive expression vector system, DNA 5 (3), 219–225.

Genes

The genes for the various subtilisins were obtained as referenced in the literature mentioned above. In particular the genes for the subtilisin 309 and 147 enzymes were obtained as described in unpublished International Patent Application No. PCT/DK 88/00002, supra.

Subtilisin Carlsberg Gene Construction

A synthetic gene was designed based on the coding sequence of the mature subtilisin Carlsberg protease and its transcription terminator (Jacobs, M., Eliasson, M., Uhlen, M. and Flock, J.-I. (1985), Cloning, sequencing and expression of subtilisin Carlsberg from *Bacillus licheniformis*). Nucleic Acids Res. 13 (24), 8913–8926), linked to the pre and pro coding sequences of the subtilisin BPN' protease (Wells, J. A., Ferrari, E., Henner, D. J., Estell, D. A. and Chen, E. Y. (1983), Cloning, sequencing and secretion of *Bacillus amyloliquefaciens* subtilisin in *Bacillus subtilis*, Nucleic Acids Res. 11 (22), 7911–7925). The gene was subdivided into seven fragments in length ranging from 127 to 313 base pairs, each fragment built up from chemically synthesized oligos of 16 to 77 nucleotides. The overlap between the oligos of the two strands was optimized in order to facilitate a one step annealing of each fragment (Mullenbach, G. T., Tabrizi, A., Blacher, R. W. and Steimer, K. S. (1986), Chemical synthesis and expression in Yeast of a gene encoding connective tissue activating peptide-III, J. Biol. Chem. 261 (2), 719–722). Each fragment was assembled and cloned in an *E. Coli* cloning and sequencing vector. Sequence analysis of these cloned fragments was performed to confirm the correctness of the sequence of each fragment. Then all of the fragments were assembled and cloned in the vector pUB110 (Lacey, R. W. and Chopra, J. (1974), Genetic studies of a multiresistant strain of *Staphylococcus aureus*, J. Med. Microbiol. 7, 285–297) and brought into *B. subtilis* DB105 (Kawamura, F. and Doi, R. H. (1984), Construction of a *Bacillus subtilis* double mutant deficient in extracellular alkaline and neutral proteases, J. Bacteriol. 160 (2), 442–444). Transcription of the gene was initiated by the HpaII promoter of the pUB110 plasmid vector (Zyprian, E. and Matzura, H. (1986), Characterization of signals promoting gene expression on the *Staphylococcus aureus* plasmid pUB110 and development of a Gram-positive expression vector system, DNA 5 (3), 219–225). In the process of the gene construction it turned out that the longest fragment (#5; 313 base pairs long) needed further fragmentation (fragments #8 and #9) in order to avoid problems with the assembly of this rather long fragment.

The amino acid sequence deduced from the nucleotide sequence differs from the earlier published subtilisin Carlsberg sequence at positions 129, 157, 161 and 212 (Smith, E. L., DeLange, R. J., Evans, W. H., Landon, W. and Markland, F. S. (1968), Subtilisin Carlsberg V. The complete sequence: comparison with subtilisin BPN'; evolutionary relationships., J. Biol. Chem. 243 (9), 2184–2191). A fifth alteration reported by Jacobs et al. (1985) could not be confirmed in the clone of the Carlsberg gene described here.

Computation of Isoelectric Point ($pI_o$)

The calculation of the isoelectric point of subtilisin 309 wild type enzyme (S000) is exemplified below in order to demonstrate the procedure used. The same procedure is applicable to the computation of any enzyme, whether it is a mutant enzyme or not.

pK values were assigned to each potentially charged amino acid residue (Tyr, Asp, Glu, Cys, Arg, His, Lys, N-terminal, C-terminal, $Ca^{2+}$). In this case the environment was taken into consideration, whereby different pK values are used for the same amino acid residue dependent on its neighbors. The assigned values are indicated in Table II.

The ratio of the occurrence of an amino acid residue at a given pH in charged or uncharged form (charged/uncharged, C/U(i)) was then calculated for both negative and positive charge, by using formulas Ia and Ib, respectively. In Table II, this ratio is only indicated for pH equal to $pI_o$.

Subsequently, the relative charge, $Q_r(i)$ or charge contribution allocated to each charged residue was calculated by using formulas IIa and IIb.

The pH value where the sum of all the charge contributions from the charged residues is equal to zero was found by iteration.

TABLE II

Calculation of isoelectric point for: S000 Subtilisin 309

| Residue | pK | Number of Residues | C/U (i)* | $Q_r(i)$ pH = 8.3 | $Q_r(i)$ pH = 10.0 | $Q_r(i)$ pH = $pI_o$ |
|---|---|---|---|---|---|---|
| Tyr | 9.9 | 3 | 2.51E–02 | –0.07 | –1.67 | –1.77 |
| Tyr | 11.6 | 2 | 5.01E–04 | 0.00 | –0.05 | –0.06 |
| Tyr | 12.5 | 2 | 6.31E–05 | 0.00 | –0.01 | –0.01 |
| Asp | 3.5 | 5 | 6.31E+04 | –5.00 | –5.00 | –5.00 |
| Glu | 4 | 5 | 2.00E+04 | –5.00 | –5.00 | –5.00 |
| C-term (Arg) | 3 | 1 | 2.00E+05 | –1.00 | –1.00 | –1.00 |
| Cys | 9.3 | 0 | 1.00E–01 | 0.00 | 0.00 | 0.00 |
| Arg | 12.8 | 8 | 3.16E+04 | 8.00 | 7.99 | 7.99 |
| His | 6.4 | 7 | 1.26E–02 | 0.09 | 0.00 | 0.00 |
| Lys | 10 | 5 | 5.01E+01 | 4.90 | 2.50 | 2.34 |
| Calcium | 20 | 1.25 | 5.01E+11 | 2.50 | 2.50 | 2.50 |
| N-term (Ala) | 8 | 1 | 5.01E–01 | 0.33 | 0.01 | 0.01 |
| Net charge | | | | 4.75 | 0.27 | 0.00 |

The calculated isoelectric point is 10.06.
* E–02 = $10^{-2}$

As indicated above and in Table II, the pK value assigned to each amino acid was different taking local variations in the environment into consideration. This results only in an enhanced precision in the calculation, but experience has shown that constant estimated pK values are helpful in showing in what direction the $pI_o$, for a given mutant enzyme will move in comparison to the $pI_o$ of the parent enzyme. This is indicated in Table III, where $pI_o$ values for estimated pK values are indicated.

In order to compare various enzymes and mutant enzymes, washing tests described in detail below have been performed. In Table III below, results from these tests using parent enzyme and mutant enzymes from subtilisin 309 (designated S000, etc.) and subtilisin carlsberg (designated C000, etc.) have been tabulated in order to demonstrate the correlation between $pI_o$ and wash performance at different pH values of the wash liquor used. In the washing tests, a low salt liquid detergent formulation of pH 8.3 according to detergent example D7 and a normal salt powder detergent of pH 10.2 according to detergent example D2 were used.

In Table III, the results are compared to the wild type enzymes (S000 and C000, respectively). In addition, the calculated and observed $pI_o$'s for the enzymes are indicated.

TABLE III

Comparative washing tests at different pH values

| Mutant | $pI_o$ calculated | $pI_o$ observed | Improvement Factor Detergent pH 8.3 | Improvement Factor Detergent pH 10.2 |
|---|---|---|---|---|
| S000 | 10.02 | 9.7 | 1 | 1 |
| S001 | 9.86 | 9.4 | 2.2 | 1 |
| S003 | 9.86 | 9.4 | 2.0 | 1 |
| S004 | 9.68 | 9.1 | 3.9 | 1 |
| S005 | 9.71 | 9.1 | 1.5 | 1 |
| S012 | 9.09 | 8.8 | 5.0 | 0.6 |
| S019 | 9.09 | 8.5 | 5.8 | 0.6 |
| S020 | 6.71 | 7.9 | 8.8 | 0.5 |
| S021 | 9.85 | — | 1.8 | 0.7 |
| S022 | 8.07 | — | 9.0 | 0.3 |
| S023 | 8.05 | — | 9.8 | 0.2 |
| S024 | 6.86 | — | 9.0 | 0.2 |
| S025 | 8.94 | — | 6.9 | 0.6 |
| S027 | 10.28 | — | 0.4 | 1.0 |
| S028 | 10.28 | — | 0.9 | 1.0 |
| S031 | 10.53 | — | 0.4 | 0.7 |
| S032 | 10.28 | — | 0.7 | — |
| S033 | 10.28 | — | 0.4 | — |
| S035 | 8.07 | — | 8.0 | 0.6 |
| S201 | 9.85 | — | 2.0 | 0.7 |
| S202 | 9.62 | — | 4.3 | 0.9 |
| S203 | 9.27 | — | 9.0 | 0.5 |
| C000 | 8.87 | — | 1 | 1 |
| C001 | 9.38 | — | 0.2 | 1.5 |
| C002 | 9.38 | — | 0.8 | 1.9 |
| C003 | 9.38 | — | 0.4 | 1.1 |
| C004 | 9.64 | — | 0.2 | 1.8 |
| C008 | 9.38 | — | 0.2 | 1.5 |

From Table III, it is seen that shifting the $pI_o$ to lower values (S-series) provides for an improvement in wash performance at low pH (pH=8.3), whereas an upward shift in $pI_o$ (C-series) provides for an improvement in wash performance at high pH (pH=10.2).

The concept of isoelectric point has thus been found to be very useful in selecting the positions of the amino acids in the parent enzyme which should be changed.

It has generally been found that mutations should be performed in codons corresponding to amino acids situated at or near to the surface of the enzyme molecule thereby retaining the internal structure of the parent enzyme as much as possible.

Purification of Subtilisins

The procedure relates to a typical purification of a 10 liter scale fermentation of the Subtilisin 147 enzyme, the Subtilisin 309 enzyme or mutants thereof.

Approximately 8 liters of fermentation broth were centrifuged at 5000 rpm for 35 minutes in 1 liter beakers. The supernatants were adjusted to pH 6.5 using 10% acetic acid and filtered on Seitz Supra S100 filter plates.

The filtrates were concentrated to approximately 400 ml using an Amicon CH2 Å UF unit equipped with an Amicon S1Y10 UF cartridge. The UF concentrate was centrifuged and filtered prior to absorption at room temperature on a Bacitracin affinity column at pH 7. The protease was eluted from the Bacitracin column at room temperature using 25% 2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step were combined and applied to a 750 ml Sephadex G25 column (5 cm dia.) equilibrated with a buffer containing 0.01 dimethylglutaric acid, 0.2 M boric acid and 0.002 M calcium chloride adjusted to pH 6.5.

Fractions with proteolytic activity from the Sephadex G25 column were combined and applied to a 150 ml CM Sepharose CL 6B cation exchange column (5 cm dia.) equilibrated with a buffer containing 0.01 M dimethylglutaric acid, 0.2 M boric acid and 0.002 M calcium chloride adjusted to pH 6.5.

The protease was eluted using a linear gradient of 0–0.1 M sodium chloride in 2 liters of the same buffer (0–0.2 M sodium chloride in case of sub 147).

In a final purification step protease containing fractions from the CM Sepharose column were combined and concentrated in an Amicon ultrafiltration cell equipped with a GR81PP membrane (from the Danish Sugar Factories Inc.).

Subtilisin 309 and mutants

Gly 195 Glu (G195E (S001));

Arg 170 Tyr (R170Y (S003));

Arg 170 Tyr+Gly 195 Glu (R170Y+G195E (S004));

Lys 251 Glu (K251E (S005));

His 120 Asp (H120D (S006));

Arg 170 Tyr+Gly 195 Glu+Lys 251 Glu (R170Y+G195E+K251E (S012));

Lys 235 Leu (K235L (S015)); His 120 Asp+Gly 195 Glu+Lys 235 Leu (H120D+G195E+K235L (S017)); His 120 Asp+Arg 170 Tyr+Gly 195 Glu+Lys 235 Leu (H120D+R170Y+G195E+K235L (S019)); and His 120 Asp+Arg 170 Tyr+Gly 195 Glu+Lys 235 Leu+Lys 251 Glu (H120D+R170Y+G195E+K235L+K251E (S020));

were purified by this procedure.

Purification of (Mutant) Subtilisin Carlsberg Proteases

Fermentation media were either directly applied on a bacitracin affinity column (5 cm diam * 15 cm; equilibrated with 10 mM Tris/HCl buffer pH 7.9; flow rate approx. 500 ml/h) or concentrated to 500 ml by means of a Nephross Andante H. F. dialyzer (Organon Technika) using a back pressure of 10–12 p.s.i. and demineralized water in the outer circuit. In the latter case, the protease was precipitated from the concentrate by adding 600 g/l ammonium sulphate. The precipitate was collected by means of centrifugation and redissolved in approx. 500 ml demineralized water. The ammonium sulphate was removed from the protease solution using the same dialyzer as described above. The final volume was approx. 300 ml, while the pH was adjusted to pH 6.0. The protease was eluted from the bacitracin columns (mentioned above) using a 10 mM Tris buffer (pH 7.9) containing 2.7 M NaCl and 18% isopropanol.

After dialysis of bacitracin-purified or concentrated protease material, further purification was accomplished by application on a CM-Trisacryl ion exchange column (5 cm. diam * 15 cm; equilibrated with 0.03M sodium phosphate pH 6.0) using a flow rate of 200 ml/h. The protease was eluted from the column with a linear gradient from 0 to 0.3 M NaCl (2*500 ml) in the phosphate buffer. Fractions containing protease activity were pooled and stored at −20° C. in the presence of buffer salts after freeze-drying.

Oligonucleotide Synthesis

All mismatch primers were synthesized on an Applied Biosystems 380 A DNA synthesizer and purified by polyacrylamide gel electrophoresis (PAGE).

Assay for Proteolytic Activity

The proteolytic activity of the mutant enzymes was assayed in order to determine how far the catalytic activity of the enzyme was retained. The determinations were performed by the dimethyl casein (DMC) method described in NOVO Publication AF 220-gb (or later editions), available from Novo-Nordisk A/S, Bagsvard, Denmark, which is incorporated herein by reference.

Assays for Wash Performance

A:

Test cloths (2.2 cm×2.2 cm, approximately 0.1 g) were produced by passing desized cotton (100% cotton, DS 71) cloth through the vessel in a Mathis Washing and Drying Unit type TH (Werner Mathis AG, Zurich, Switzerland) containing grass juice.

Finally, the cloth was dried in a strong air stream at room temperature, stored at room temperature for 3 weeks, and subsequently kept at −18° C. prior to use.

All tests were performed in a model miniwash system. In this system, six test cloths were washed in a 150 ml beaker containing 60 ml of detergent solution. The beakers were kept in a thermostat water bath at 30° C. with magnetic stirring.

The following standard liquid detergent was used:

| | | |
|---|---|---|
| AE, Berol 160 | 15% | |
| LAS, Nasa 1169/F | 10% | |
| Coconut fatty acid | 9% | |
| Oleic acid | 1% | |
| Triethanolamine | 9% | |
| Glycerol | 1.5% | |
| Ethanol | 8% | |
| Tri.Na.Citrat.2H$_2$O | 0.1% | |
| CaCl.2H$_2$O | 0.1% | |
| NaOH | 1% | |
| Water from LAS | 23.3% | |
| Water from glycerol | 1.5% | |
| Water added | 34.9% | |

The percentages given are the percentage of active content.

The pH was adjusted with 1 N NaOH to 8.14. The water used was ca. 6° dH (German Hardness).

Tests were performed at enzyme concentrations of: 0, 1.0 mg enzyme protein/l and 10.0 mg enzyme protein/l, and two independent sets of tests were performed for each of the mutants. The results shown in the following are means of these tests.

The washings were performed for 60 minutes and the cloths were then flushed in running tap-water for 25 minutes in a bucket.

The cloths were then air-dried overnight (protected against daylight) and the remission, R, was determined on an ELREPHO 2000 photometer from Datacolor S. A., Dietkikon, Switzerland at 460 nm.

As a measure of the wash performance, differential remission, delta R, was used. Differential remission is equal to the remission after wash with enzyme added minus the remission after wash with no enzyme added.

B:

The wash performance of various mutants was tested against grass juice stained cotton cloths according to the method described above.

2.0 g/l of a commercial US liquid detergent was used.

The detergent was dissolved in a 0.005 M ethanolamine buffer in ion-exchanged water. The pH was adjusted to pH 8.0, 9.0, 10.0 and 11.0 respectively with NaOH/HCl.

The temperature was kept at 30° C. isothermic for 10 min.

The mutants were dosed at 0.25 mg enzyme protein/l each.

C:

Washing tests using the detergent compositions exemplified in the detergent examples below were performed in a mini washer utilizing cotton based test cloths containing pigments, fat and protein (casein). The conditions were:

a) 2 g/l detergent D3 in 6°fH (French hardness) water at pH 8.3 or b) 5 g/l detergent D2 in 15°fH water at pH 10.2.

After rinsing and drying, reflection at 460 nm was measured.

The improvement factor was calculated from a dose-response curve and relates to the amount of enzyme needed for obtaining a given delta R value in comparison to the wild type enzyme in question (S000 and C000), meaning that an improvement factor of 2 indicates that only half the amount of enzyme is needed to obtain the same delta R value.

The results of these tests are shown in Table III above.

D:

Experimental tests of lipase stability were carried out for example using the following materials:

1 LU/ml Pseudomonas cepacia lipase was incubated in wash liquor of each of two types, O and W (described below). Aliquots were taken at intervals and tested for lipase activity. Parallel incubations were carried out without protease or with protease of various types as noted below, to test the effect of the protease on the retention of lipase activity. Wild-type proteases were tested at 20 GU/ml, mutated proteases were tested at 0.5 microgram/ml.

Detergent Compositions Comprising Enzyme Variants

The invention is illustrated by way of the following non-limiting Examples:

Detergent D1:

A detergent powder is formulated to contain: total active detergent about 16%, anionic detergent about 9%, nonionic detergent about 6%, phosphate-containing builder about 20%, acrylic or equivalent polymer about 3.5% (alternatively down to about 2%), perborate bleach precursor about 6–18%, alternatively about 15–20%, amino-containing bleach activator about 2%, silicate or other structurant about 3.5%, alternatively up to about 8%, enzyme of about 8 glycine units/mg activity, with alkali to adjust to desired pH in use, and neutral inorganic salt and enzymes (about 0.5% each enzyme).

The anionic detergent is a mixture of sodium dodecylbenzene sulphonate, alternatively sodium linear alkylbenzene-sulphonate, 6% and primary alkyl sulphate 3%. The nonionic detergent is an ethoxylate of an approx. C13–C15 primary alcohol with 7 ethoxylate residues per mole. The phosphate builder is sodium tripolyphosphate. The polymer is polyacrylic acid, alternatively acrylic/maleic copolymer. The perborate bleach precursor is sodium tetraborate tetrahydrate or monohydrate. The activator is tetraacetylethylenediamine. The structurant is sodium silicate. The neutral inorganic salt is sodium sulphate.

The enzymes comprise protease according to Mutant S001, alternatively protease S003, S004, S005, C001, C002, C003, C004, C005, C008, S015, S017, S021, S226, S223, S224 or S225.

Detergent D1a:

A detergent powder is formulated to contain: total active detergent about 15%, anionic detergent about 7%, nonionic detergent about 6%, phosphate-containing builder about 25%, acrylic or equivalent polymer about 0.5%, perborate bleach precursor about 10%, amino-containing bleach activator about 2%, silicate or other structurant about 6%, protease enzyme of about 8 glycine units/mg grade, with alkali to adjust to desired pH in use, and neutral inorganic salt and enzymes (about 0.5% each enzyme).

The anionic detergent is sodium linear alkyl-benzene-sulphonate. The nonionic detergent is an ethoxylate of an approx. C13–C15 primary alcohol with 7 ethoxylate residues per mole or a mixture of this with the corresponding alcohol ethoxylated to the extent of 3 residues per mole. The phosphate builder is sodium tripolyphosphate. The perborate or peracid bleach precursor is sodium tetraborate tetrahydrate. The activator is tetraacetylethylenediamine. The structurant is sodium silicate. The neutral inorganic salt is sodium sulphate. The enzymes comprise protease according to Mutant S001, alternatively S003, S004, S005, C001, C002, C003, C004, C005, C008, S015, S017, S021 or S226.

Detergent D2:

A detergent powder is formulated to contain: total active detergent about 16%, anionic detergent about 9%, nonionic detergent about 6%, zeolite-containing builder about 20%, acrylic or equivalent polymer about 3.5%, perborate bleach precursor about 6–18%, amino-containing bleach activator about 2%, silicate or other structurant about 3.5%, alternatively down to about 2.5%, enzyme of about 8 (alternatively about 15) glycine units/mg grade, with alkali to adjust to desired pH in use, and neutral inorganic salt and enzymes (about 0.5% each enzyme).

The anionic detergent is a mixture of sodium dodecyl-benzene sulphonate, alternatively sodium linear alkyl-benzene-sulphonate, 6% and primary alkyl sulphate 3%. The nonionic detergent is an ethoxylate of an approx. C13–C15 primary alcohol with 7 ethoxylate residues per mole. The zeolite builder is type A zeolite. The polymer is polyacrylic acid. The perborate bleach precursor is sodium tetraborate tetrahydrate or monohydrate. The activator is tetraacetylethylenediamine. The structurant is sodium silicate. The neutral inorganic salt is sodium sulphate. The enzymes comprise protease according to Mutant S001, alternatively S003, S004, S005, C001, C002, C003, C004, C005, C008, S015, S017, S021 or S226.

Detergent D2a:

A detergent powder is formulated to contain: total active detergent about 14%, anionic detergent about 7%, nonionic detergent about 7%, zeolite-containing builder about 25%, acrylic or equivalent polymer about 3%, perborate or peracid bleach precursor about 10%, amino-containing bleach activator about 2%, silicate or other structurant about 0.5%, enzyme of about 6 glycine units/mg grade, with alkali to adjust to desired pH in use, and neutral inorganic salt and enzymes (about 0.5% each enzyme).

The anionic detergent is sodium linear alkyl-benzene-sulphonate, the nonionic detergent is a mixture of ethoxylates of an approx. C13-C15 primary alcohol with 7 and 3 ethoxylate residues respectively per mole. The zeolite builder is type A zeolite. The polymer is an acrylic/maleic copolymer. The perborate bleach precursor is sodium tetraborate monohydrate. The activator is tetraacetylethylenediamine. The structurant is sodium silicate. The neutral inorganic salt is sodium sulphate. The enzymes comprise protease according to Mutant S001, alternatively S003, S004, S005, C001, C002, C003, C004, C005, C008, S015, S017, S021 or S226.

Detergent D3:

An aqueous detergent liquid is formulated to contain: Dodecylbenzene-sulphonic acid 16%, C12–C15 linear alcohol condensed with 7 mol/mol ethylene oxide 7%, monoethanolamine 2%, citric acid 6.5%, sodium xylenesulphonate 6%, sodium hydroxide about 4.1%, protease 0.5%, minors and water to 100%. The pH is adjusted to a value between 9 and 10. The enzyme is a protease according to Mutant S020, alternatively S019, S012, S004, S001, S003, S005, S015, S017, S021, S022, S025, S035, S201, S223-6 or S235.

Detergent D4:

A nonaqueous detergent liquid is formulated using 38.5% C13–C15 linear primary alcohol alkoxylated with 4.9 mol/mol ethylene oxide and 2.7 mol/mol propylene oxide, 5% triacetin, 30% sodium triphosphate, 4% soda ash, 15.5% sodium perborate monohydrate containing a minor proportion of oxoborate, 4% TAED, 0.25% EDTA of which 0.1% as phosphonic acid, Aerosil 0.6%, SCMC 1% and 0.6% protease. The pH is adjusted to a value between 9 and 10, e.g. about 9.8. The enzyme comprises protease according to Mutant S001, alternatively S003, S004, S021, S035, S201, S225, S226 or S235.

Detergent D5:

A detergent powder is formulated in the form of a granulate having a bulk density of at least 600 g/l, containing about 20% by weight surfactant of which about 10% is sodium dodecylbenzene sulphonate and the remainder is a mixture of Synperonic A7 and Synperonic A3 (about 5.5% to 4.5%) and zero neutral inorganic salt (e.g. sodium sulphate), plus phosphate builder about 33%, sodium perborate tetrahydrate about 16%, TAED activator about 4.5%, sodium silicate about 6% and minors including sodium carbonate about 2% and moisture content about 10%. Enzymes (about 0.5% each enzyme) are included. The enzyme comprises protease according to Mutant S001, alternatively S003, S004, S005, C001, C002, C003, C004, C005, C008, S223, S224, S225, S226 or S235.

Detergent D6:

A detergent powder is formulated in the form of a granulate having a bulk density of at least 600 g/l, alternatively about 550 g/l, containing about 20%, alternatively down to about 16%, by weight surfactant of which about 9%, alternatively about 7%, is sodium dodecylbenzene sulphonate, alternatively sodium linear alkyl benzene sulphonate and the remainder is a mixture of Synperonic A7 and Synperonic A3 (or similar ethoxylates) (respectively about 5% & 6%, alternatively about 4% and 7%) and zero neutral inorganic salt (e.g. sodium sulphate), plus zeolite builder about 30%, alternatively about 25%, sodium perborate tetrahydrate, alternatively monohydrate, about 14% or 15%, TAED activator about 3.6% and minors including sodium carbonate about 9%, or up to 15%, Dequest® 2047 about 0.7% and moisture content about 10%. Enzymes (about 0.5% each enzyme, or about 0.2% lipase and about 0.7% protease) are included. The enzyme comprises protease according to Mutant S001, alternatively S003, S004, S005, C001, C002, C003, C004, C005, C008, S223, S224, S225, S226 or S235.

Detergent D6a:

A detergent powder is formulated in the form of a granulate having a bulk density of at least 600 g/l, containing about 15% by weight surfactant of which about 7% is sodium linear alkyl benzene sulphonate, 2% primary alcohol sulphate and the remainder Synperonic A7 or similar ethoxylate and zero neutral inorganic salt (e.g. sodium sulphate), plus zeolite builder about 22%, sodium perborate tetrahydrate about 15%, TAED activator about 7% and minors including sodium carbonate about 15t, Dequest®

2047 about 0.7% and moisture content about 10%. Enzymes (about 1.2%) include protease according to Mutant S001, alternatively S003, S004, S005, C001, C002, C003, C004, C005, C008, S223, S224, S225, S226 or S235.

Detergent D7:

A detergent powder is formulated to contain: Dodecyl-benzenesulphonic acid 6%, C12–C15 linear alcohol condensed with 7 mol/mol ethylene oxide 5%, fatty acid soap 3%, Sokolan® CP5 polymer 3%, zeolite A 22%, sodium carbonate 10%, sodium sulphate 17%, clay particles 8%, sodium perborate tetrahydrate 13%, tetraacetylethylenediamine 2%, protease 0.5%, minors and water to 100%. The pH is adjusted to a value between 9 and 10. The protease enzyme comprises protease according to Mutant S001, alternatively S003, S004, S005, C001, C002, C003, C004, C005, C008, S223, S224, S225, S226 or S235.

Detergent D8:

A detergent (soap) bar according to an embodiment of the invention is formulated as follows: soap based on pan-saponified 82% tallow, 18% coconut oil, neutralized with 0.15% orthophosphoric acid, mixed with protease (about 8 GU/mg of the bar composition) and with sodium formate 2%, borax 2%, propylene glycol 2% and sodium sulphate 1%, is then plodded on a soap production line. The protease enzyme comprises protease according to Mutant S001, alternatively S003, S004, S005, C001, C002, C003, C004, C005, C008, S021, S025, S035, S201, S202, S223, S224, S225, S226 or S235.

Detergent D9:

Structured liquid detergents can for example contain, in addition to a protease as described herein, 2–15% nonionic surfactant, 5–40% total surfactant, comprising nonionic and optionally anionic surfactant, 5–35% phosphate-containing or non-phosphate containing builder, 0.2–0.8% polymeric thickener, e.g. cross-linked acrylic polymer with m.w. over $10^6$, at least 10% sodium silicate, e.g. as neutral waterglass, alkali (e.g. potassium-containing alkali) to adjust to a desired pH, preferably in the range 9–10 or upwards, e.g. above pH 11, with a ratio sodium cation: silicate anion (as free silica) (by weight) of less than 0.7:1 and viscosity of 0.3–30 Pas (at 20° C. and $20^{s-1}$).

Suitable examples contain about 5% nonionic surfactant C13–15 alcohol alkoxylated with about 5 EO groups and about 2.7 PO groups per mole, 15–23% neutral waterglass with 3.5 weight ratio between silica and sodium oxide, 13–19% KOH, 8–23% STPP, 0–11% sodium carbonate, 0.5% Carbopol® 941.

Protease (e.g. 0.5%) includes Mutant S001, alternatively S021, S025, S035, S201, S202, S223, S224, S225, S226 or S235.

Detergent D10:

A structured, viscous, aqueous liquid detergent suitable for laundry use is formulated as follows (% by weight):

| | |
|---|---|
| Citric acid | 2.5 |
| Borax (10 aq) | 4 |
| NaOH | 2 |
| Glycerol | 5 |
| C14–C15 Linear alkyl-benzene-sulphonate, or C14–15 primary alcohol sulphate | 6.5 |
| Synperonic A3 Nonionic C12–C15 3EO | 1.2 |
| Synperonic A7 Nonionic C12–C15 7EO | 3.6 |
| Zeolite | 20 |
| Protease | 0.5 |
| Amylase (Termamyl ® 300LDX) | 0.2 |
| minors and water | to 100% |

The pH can be adjusted to a value between 9 and 10. The enzyme comprises protease Mutant S020, alternatively S019, S012, S004, S001, S003, S005, S021, S035, S201, S223-6 or S235.

Detergent D11:

An isotropic aqueous liquid detergent suitable for laundry use is formulated as follows (% by weight):

| | |
|---|---|
| Citric acid | 2 |
| Boric acid | 1 |
| NaOH | 3 |
| KOH | 4.5 |
| Glycerol | 10 |
| Ethanol | 6.5 |
| Nonionic surfactant (C12-alcohol 6.5EO ethoxylate groups/mol) or sodium primary alcohol sulphate | 10 |
| Oleic acid | 16 |
| Coconut oil (C12) soap | 1.1 |
| Protease | 0.5 |
| minors and water | to 100% |

The pH can be adjusted to a value between 9 and 10. The enzyme comprises protease Mutant S020, alternatively S019, S012, S004, S001, S003, S005, S021, S025, S035, S201, S223-6 or S235.

Detergent D12:

An aqueous liquid detergent composition is formulated to contain:

| | |
|---|---|
| sodium alkyl-benzene-sulphonate | 14.5 |
| C18 sodium soap | 2 |
| Nonionic detergent (C12–15 6EO) | 9 |
| Fatty acid (oleic acid) | 4.5 |
| sodium alkenyl succinate | 11 |
| propanediol | 1.5 |
| ethanol | 3.6 |
| sodium citrate | 3.2 |
| Complexing agent e.g. Dequest 2060 | 0.7 |
| Protease | 0.5 |
| Amylase | 0.1 |
| Sodium chloride | 0.5 |
| minors and water | to 100% |

The pH can be adjusted to a value between 9 and 10. The enzyme comprises protease Mutant S020, alternatively S019, S012, S004, S001, S003, S005, S021, S025, S035, S201, S202, S223-6 or S235.

Detergent D13:

An aqueous liquid detergent composition is formulated to contain:

| | |
|---|---|
| sodium alkyl-benzene-sulphonate | 14.5 |
| sodium alkyl-benzene-sulphonate | 8 |
| nonionic detergent 6.5EO | 10 |
| Oleic diethylamide | 10 |
| Fatty acid (C12/C18 75:25) | 18 |
| sodium citrate | 1 |
| triethanolamine | 5 |
| propanol | 7 |
| ethanol | 5 |
| Dequest 2060 | 0.5 |
| Protease | 0.5 |
| Amylase | 0.1 |
| minors and water | to 100% |

The pH can be adjusted to a value between 9 and 10. The enzyme comprises protease Mutant S020, alternatively S019, S012, S004, S001, S003, S005, S021, S025, S035, S201, S202, S223-6 or S235.

Detergent D14:

A non-aqueous liquid detergent composition is formulated to contain (% by weight):

| | |
|---|---|
| Liquid nonionic detergent (C10–12, 6.2EO) | 41% |
| triacetin | 5 |
| linear alkylbenzenesulphonic acid | 6 |
| magnesium oxide stabilizer | 1 |
| Sodium carbonate builder/base | 18 |
| Calcium carbonate builder | 8 |
| bleach activator TAED | 3.5 |
| bleach precursor perborate monohydrate | 10.5 |
| partly-hydrophobic silica | 2 |
| protease | 0.4 |
| lipase (Lipolase ®) | 3 |
| minors or additional liquid nonionic surfactant (no water) | to 100% |

In formulating this composition, the liquid nonionic surfactant and triacetin are added first, followed by the magnesium oxide, then the other ingredients except enzyme. The mixture is milled in a colloid mill and cooled and finally the enzyme(s) and any other heat-sensitive minors are added.

The enzyme comprises protease Mutant S020, alternatively S019, S012, S004, S001, S003, S005, S021, S025, S035, S201, S202, S223-6 or S235.

Any one of the detergent formulations described and exemplified in EP 0 342 177 also may be used in conjunction with Mutant as for detergent D3.

RESULTS

Generation of Site-specific Mutations of the Subtilisin 309 Gene

Site specific mutations were performed by the method of Morinaga et al. (Biotechnology, supra). The following oligonucleotides were used for introducing the mutations:

a) Gly 195 Glu (G195E (S001)):

A 27-mer mismatch primer, Nor-237, which also generates a novel SacI restriction site:

5' CACAGTATGGGCGCAGGGCTTGACAT-TGTCGCACCAGG 3' Nor-237 5' GTATGGCGCA-GAGCTCGACATTTGTCGC 3'

SacI b) Arg 170 TYr (R170Y (S003)):

A 25-mer mismatch primer, Nor-577, which destroys a HaeIII site:

HaeIII

5' GCTATCCGGCCCGTTATGCGAACGC 3' Nor-577 3' CGATAGGCCGTATAATACGCTTGCG 5' c) His 120 Asp (H120D (S006)):

A 32-mer mismatch primer, Nor-735, which destroys a SphI site:

SDhI

5' AGGGAACAATGGCATGCACGTTGCTAATTTGA 3' Nor-735 5' AGGGAACAATGGCATGGACGT-TGCTAATTTGA 3' d) Lvs 251 Glu (K251E (S005)):

A 32-mer mismatch primer, Nor-736, which generates a XhoI site:

5' CAAATCCGCAATCATCTAAAGAATACGGCAAC 3' Nor-736 5' CAAATCCGCAATCATCTC-GAGAATACGGCAAC 3'

XhoI e) LYs 235 Leu (K235L (S015)):

A 24-mer mismatch primer, Nor77-856, which generates a PstI site:

5' GCCCTTGTTAAACAAAAGAACCCA 3' Nor-856 5' GCCCTTGTTCTGCAGAAGAACCCA 3'

PstI f) Arg 170 Tyr; GlY 195 Glu (R170Y;G195E (S004)):

A combination of Nor-577 and Nor-237 was performed in analogy with the above.

g) Gly 195 Glu; Lys 251 Glu (G195E;K251E (S018)):

A combination of Nor-237 and Nor-736 was performed in analogy with the above.

h) Arg 170 Tyr; Lvs 251 Glu (R170Y;K251E (S011)):

A combination of Nor-577 and Nor-736 was performed in analogy with the above.

i) Ara 170 Tyr; Gly 195 Glu; Lys 251 Glu (R170Y;G195E;K251E (S012)):

A combination of Nor-577, Nor-237 and Nor-736 was performed in analogy with the above.

j) Gly 195 Glu; Lys 235 Leu (G195E;K235L):

A combination of Nor-237 and Nor-856 was performed in analogy with the above.

k) Arg 170 Tyr; Gly 195 Glu; Lys 235 Leu (R170Y:G195E;K235L):

A combination of Nor-577, Nor-237 and Nor-856 was performed in analogy with the above.

l) His 120 Asp; Lvs 235 Leu (H120D;K235L (S016)):

A combination of Nor-735 and Nor-856 was performed in analogy with the above.

m) His 120 Asp; Gly 195 Glu; Lys 235 Leu (H120D: G195E; K235L (S017)):

A combination of Nor-735, Nor-237 and Nor-856 was performed in analogy with the above.

n) His 120 Asp; Ara 170 Tyr; Glv 195 Glu; Lys 235 Leu (H120D; R170Y; G195E; K235L (S019)):

A combination of Nor-735, Nor-577, Nor-237 and Nor-856 was performed in analogy with the above.

o) His 120 Asp; Arg 170 Tyr; Gly 195 Glu; Lys 235 Leu; Lys 251 Glu (H120D; R170Y; G195E: K235L; K251E (S020):

A combination of Nor-735, Nor-577, Nor-237, Nor-856 and Nor-736 was performed in analogy with the above.

Gapped duplex mutagenesis was performed using the plasmids pSX93, pSX119 and pSX120 as templates.

pSX93 is shown in FIG. 3 and is pUC13 (Vieira, J. and Messing, J.: 1982, Gene 19: 259–268) harboring an 0.7 kb XbaI-HindIII fragment of the subtilisin 309 gene including the terminator inserted in the polylinker. the plasmid pSX119 was used for the introduction of mutations in the N-terminal part of the enzyme. pSX119 is pUC13 harboring an EcoRI-XbaI fragment of the subtilisin 309 gene inserted into the polylinker. The templates pSX93 and pSX119 thus cover the whole of the subtilisin 309 gene.

Plasmid pSX120 is a plasmid where the HpaI-HindIII fragment with the subtilisin 309 gene from pSX88 is inserted into EcoRV-HindIII on pDN 1681, in a way whereby the protease gene is expressed by the amy M and amy Q promotors. pDN 1681 is obtained from pDN 1380 (Diderichsen, B. and Christiansen, L.: 1988, FEMS Microbiology Letters 56: 53–60) with an inserted 2.85 bp ClaI fragment from *B. amyloliquefaciens* carrying the amy Q gene with promotor (Takkinen et al.: 1983, J. Biol. Chem. 258: 1007ff.). The construction of pSX120 is outlined in FIG. 1, showing that pDN1681 is cut with EcoR5 and HindIII and pSX88 with HindIII and HpaI, whereafter ligation results in pSX120 regulated by the amy M and amy Q promotors.

Four further plasmids pSX170, pSX172, pSX173 and pSX186 were constructed for gapped duplex mutagenesis of the subtilisin 309 gene:

pSX170: SphI-KpnI, 700 bp from pSX120 inserted into pUC 19 SphI-KpnI, from amino acid residue 170 in mature subtilisin 309 to terminator.

pSX172: EcoRI-SphI, 1360 bp from pSX120 inserted into pUC 19 EcoRI-SphI, from the promoter to amino acid residue 170 in mature subtilisin 309.

pSX173: like pSX170, but with G195E.

pSX186: PvuII-EcoRI, 415 bp from pSX120 inserted into pUC 19 HincI-EcoRI, from amino acid residue 15 to amino acid residue 206 in mature subtilisin 309.

Figure 2:
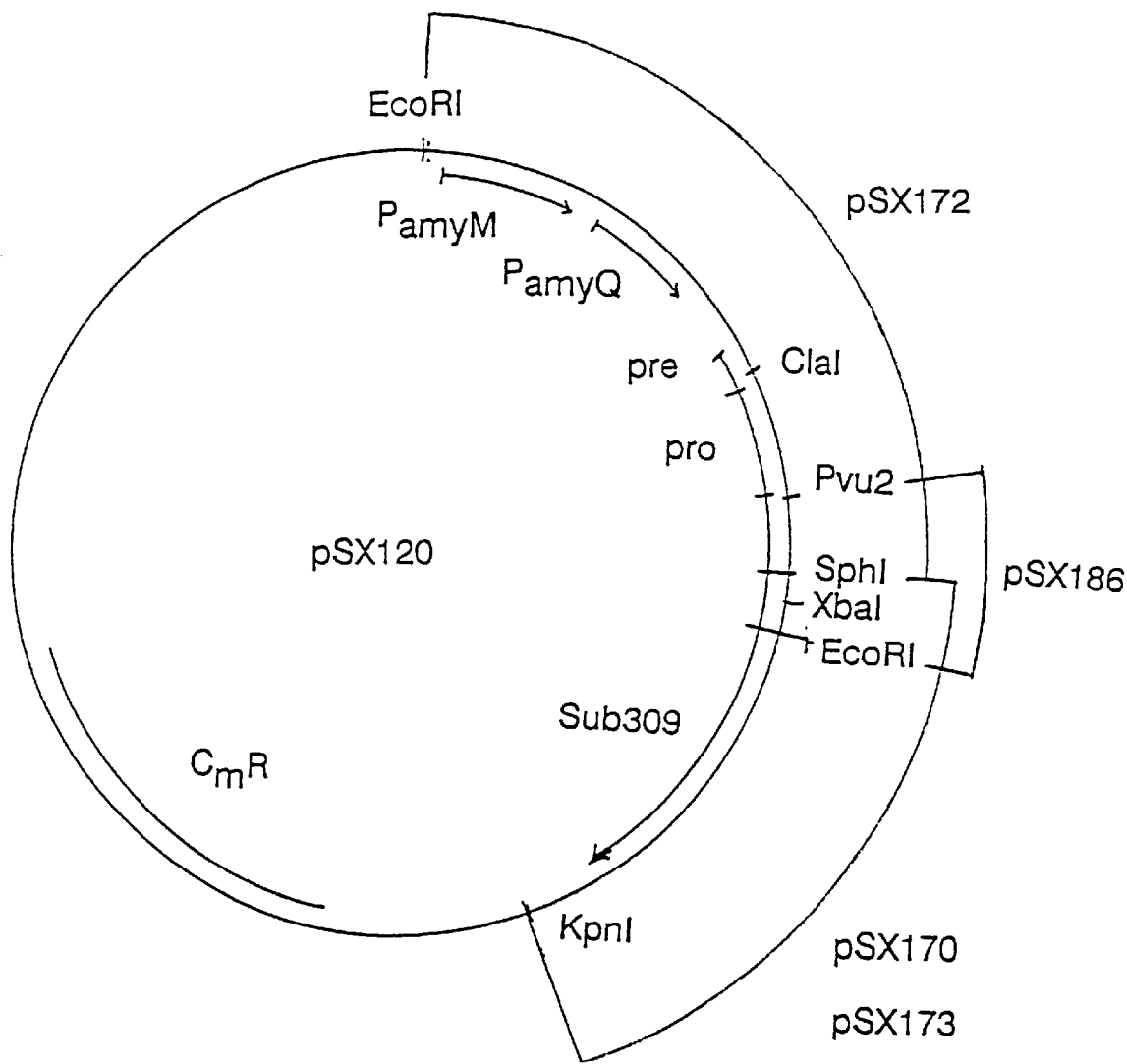
FIG. 2 shows a restriction map of plasmid pSX88.

FIG. 2 shows a somewhat detailed restriction map of pSX120 on which it is indicated which fragments were used for the construction of plasmids pSX170, pSX172, pSX173 and pSX186.

The mutation a) was performed by cutting pSX93 with XbaI and ClaI as indicated in FIG. 3 and described in the section "GENERATION OF SITE DIRECTED MUTATIONS IN THE SUBTILISIN GENE" and in unpublished International Patent Application No. PCT/DK 88/00002, supra.

Mutations b), d) and e) were performed correspondingly by cutting pSX170 by SphI and KpnI.

Mutations f) and g) were performed as above, but with pSX173 instead of pSX170.

Mutation c) was performed correspondingly by cutting pSX186 by PstI and EcoRI.

The mutations h) to o) were constructed by combining DNA fragments with single or double mutations b) to g) using the restriction sites NheI, XbaI, ClaI, AvaII and KpnI as appropriate.

Further mutants were produced using similar methods or general methods as known from the literature.

Subtilisin Carlsberg Mutants

For certain examples of mutations in subtilisin Carlsberg mentioned in this specification the following changes in the nucleotide sequence of the gene were introduced:

Asp 14 Lys (D14K (C001)) (GAT→AAG)

Asp 120 Lys (D120K (C002)) (GAT→AAA)

Asp 140 Lys (D140K (C003)) (GAC→AAA)

Asp 14 Lys+Asp 120 Lys (D14K+D120K (C004))

Lys 27 Asp (K27D (C005)) (AAA→GAT)

Lys 27 Asp+Asp 120 Lys (K27D+D120K (C006))

Asp 172 Lys (D172K (C008)) (GAC→AAA)

Asp 14 Lys+Asp 120 Lys+Asp 140 Lys+Asp 172 Lys (D14K+D120K+D140K+D172K (C010))

Val 51 Asp (V51D (C100))

Glu 54 Thr (E54T (C101)) (GGG→ACA)

Glu 54 Tyr (E54Y (C102)) (GGG→TAT)

These changes were introduced by changing the corresponding oligos in the fragments concerned. The correctness of the new sequences was confirmed after which the original oligos were replaced by these new sequences and assembled into new DNA fragments. Finally, the fragments were reassembled into the new subtilisin Carlsberg gene.

Expression of Mutant Subtilisins

Subsequent to sequence confirmation of the correct mutation, the mutated DNA fragments were inserted into plasmid pSX92 or pSX120, which were used for producing the mutants.

Figure 4:
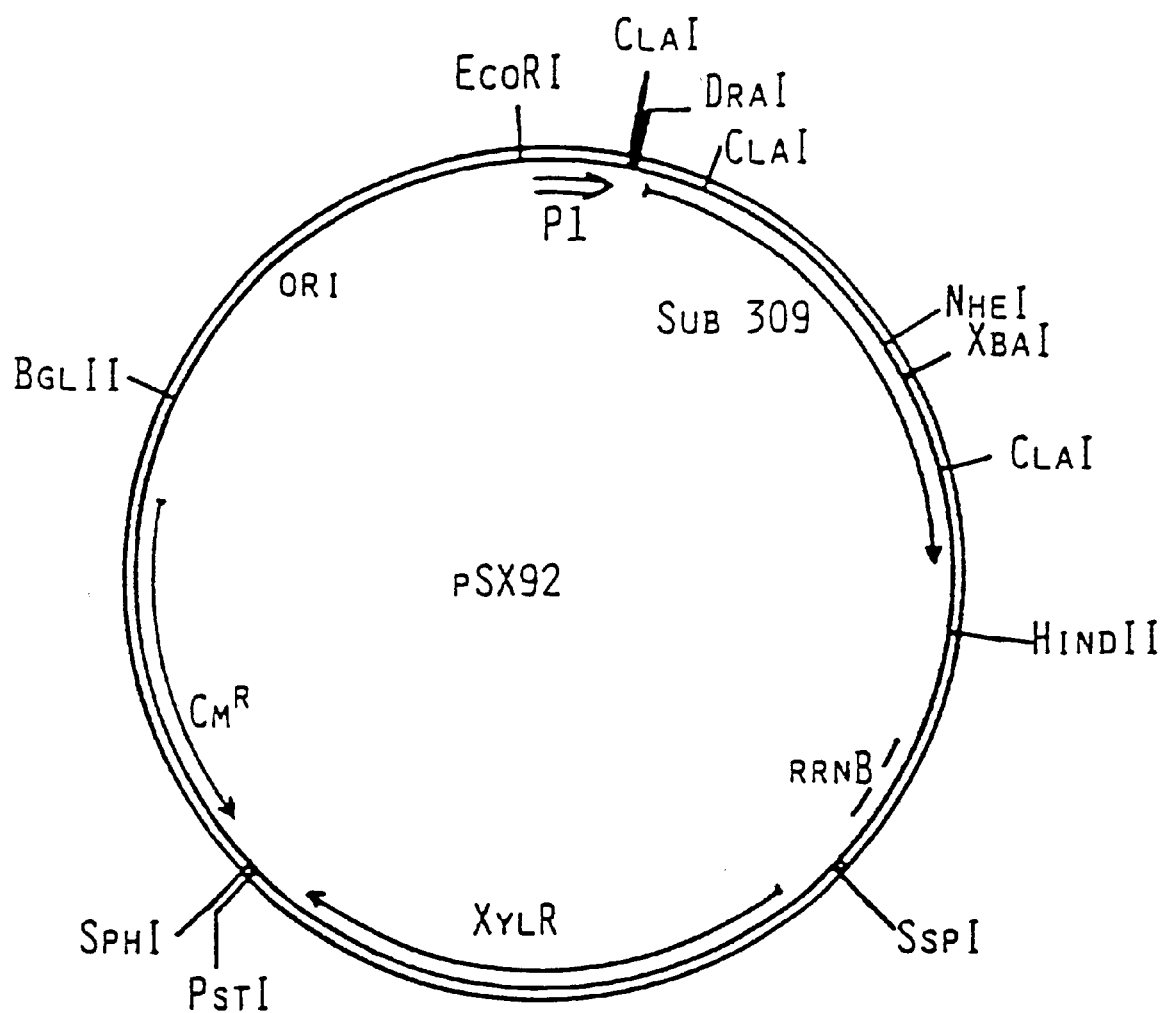
FIG. 4 shows the restriction map for plasmid pSX92.

Plasmid pSX92 is shown in FIG. 4 and was produced by cloning the Sub 309 gene into plasmid pSX62 cut at ClaI, filled in with the Klenow fragment of DNA polymerase I and cut with HindIII prior to the insertion of the fragments DraI-NheI and NheI-HindIII from the cloned Sub 309 gene.

To express the mutants, the mutated fragments (XbaI-ClaI, XbaI-HindIII, or EcoRI-XbaI) were excised from the appropriate mutation plasmid pSX93, pSX119, pSX170, pSX172, pSX173 and pSX186, respectively, and inserted into pSX92 or pSX120 to obtain plasmids capable of expressing the various mutants.

The mutated pSX92 or pSX120 was then used to transform B. subtilis DN497.

The transformed cells were then spread on LB agar plates with 10 mM phosphate, pH 7, 6 µg/ml chloramphenicol and 0.2% xylose to induce the xyn-promoter in the plasmid. The plates also contained 1% skim milk so that the protease producing transformants could be detected by the clear halo where the skim milk had been degraded.

After appropriate growth, the mutated enzymes were recovered and purified.

Fermentation of the Subtilisin Carlsberg Species

In order to produce protease enzyme on the basis of the microorganisms carrying mutant genes for BPN' as described above, a Rushton-type Chemoferm fermenter was generally used with an eight flat blade impeller and a working volume of 8 liters. The fermenter configuration was prepared conform to the safety regulations for VMT and consisted of:

a) A pressure controller (type 4-3122, Bell & Howell) cutting off air supply above 0.1 bar overpressure. This is done to prevent clogged exhaust air filters.

b) A foam trap on the gas outlet made from a 20 l suction vessel having anti-foam on the bottom.

c) A cooling water jacket without seals in order to prevent contamination of the cooling water or tapwater drain.

d) An absolute exhaust filter is used (Gelman acro 50, 0.45 micron).

e) Sampling via a sampling pump device with a small internal volume.

Controls

Gas flows were controlled using mass-flow meters (Brooks, type 5852, range 0–10 l).

The pH was controlled using a Hartmann and Braun transmitter and a Philips controller (Witromat). Concentrated NaOH (3M) was used as a neutralizer.

Exhaust gases were analyzed using a Unor 4N (C02) and an Oxygor 7N (O2) from Maihak, Westinghouse. Oxygen tension in the medium was determined using an industrial polarographic sterilizable oxygen probe (Ingold type 322756702).

The medium temperature was monitored using a PT100 sensor and a Honeywell temperature controller (class 84). Foaming was kept at an acceptable level using a contact electrode, while a level switch activated an anti-foam dosage pump.

All external controls were put under the control of a Hewlett Packard microcomputer (HP220).

Cultivation Conditions

The inocula were prepared by incubating a shake flask culture at 30° C. for 16h at 250 rpm in a rotary shaker (LH fermentation, type MKx). 300 ml inoculum was used for 8L medium being conditioned at the actual fermentation conditions (pH 7.0, 30° C., air flow 3.5 l/min, stirrer 1000–1500 rpm). Dissolved oxygen concentration was kept 25% above air saturation. Anti foaming agent used was a silicon oil based material (Rhodorsil R426, Rhone Poulenc).

Production of Subtilisin Protease

The (mutant) proteases were produced using the B. subtilis DB105 strain containing the mutant gene as described under gene construction. The culture medium consists of: 8 g/l $NH_4Cl$; 4 g/l $KH_2PO_4$; 4 g/l $K_2HPO_4$; 2 g/l NaCl; 1 g/l $MgSO_4.2H_2O$; 10 g/l yeast extract; and 40 g/l sucrose. The pH was adjusted to 7.0, and sterilization was performed for 45 min at 120° C. After sterilization, 25 mg/l tryptophan and 20 mg/l Neomycin were added. Fermentations were stopped after 20–30 hours. The media were cleared from cells by centrifugation.

Proteolytic Activity of Mutant Subtilisins

The proteolytic activity of various mutants was tested against casein as protein substrate, according to the DMC method supra. The results are presented in Table IV.

From the table it is seen that mutant S005 exhibits a slightly enhanced activity compared to the parent S000, whereas the remaining mutants exhibit a slightly decreased activity.

TABLE IV

Proteolytic Activity of Mutant Subtilisins

| Mutant | Relative Activity |
| --- | --- |
| None (S000) | 100 |
| S001 | 95 |
| S003 | 90 |
| S004 | 85 |
| S005 | 105 |
| S006 | 100 |
| S012 | 80 |
| S017 | 90 |
| S019 | 70 |
| S020 | 75 |
| S024 | 70 |

Wash Performance of Mutant Subtilisins

A:

The wash performance of various mutants in the standard liquid detergent of pH 8.14 was tested in a model system against grass juice according to the methods detailed supra. The results are presented in table V.

TABLE V

| | Delta R values: Enzyme Concentration | |
| --- | --- | --- |
| Mutant | 1.0 mg/l | 10.0 mg/l |
| S000 | 4.0 | 10.7 |
| S001 | 5.9 | 12.8 |
| S003 | 6.0 | 13.5 |
| S004 | 5.8 | 13.0 |
| S012 | 4.2 | 9.6 |
| S019 | 10.5 | 19.4 |
| S020 | 9.4 | 18.6 |

From the table it is seen that all of the tested mutants exhibited improved or equal wash performance compared to the wild type parent enzyme. The wash performance of the mutants 019 and S020 is improved so that 1.0 mg/l of these enzymes roughly stated should be able to replace 10.0 mg/l of the wild type parent enzyme, thereby indicating a substantial improvement in the wash performance for the mutant enzymes of the invention.

B:

The results from tests of some of the enzyme variants of the invention in the modified commercial US liquid detergent at various pH values in a model system are shown in Table VI.

TABLE VI

Wash performance at different pH's

| | | Delta R pH | | | |
| --- | --- | --- | --- | --- | --- |
| Mutant | pI$_o$ | 8.0 | 9.0 | 10.0 | 11.0 |
| S000 | 10.02 | 1.4 | 2.6 | 3.1 | 10.1 |
| S001 | 9.86 | 2.1 | 4.0 | 6.6 | 14.0 |
| S003 | 9.86 | 2.3 | 5.0 | 8.1 | 14.1 |
| S004 | 9.68 | 4.1 | 9.7 | 11.7 | 10.9 |
| S005 | 9.71 | 2.2 | 4.3 | 6.3 | 13.9 |
| S012 | 9.09 | 5.7 | 11.9 | 13.8 | 6.3 |
| S019 | 9.09 | 6.4 | 10.7 | 12.2 | 3.7 |
| S020 | 6.71 | 7.8 | 10.6 | 8.5 | 2.4 |

The results clearly show that shifting the pI$_o$ of an enzyme to the pH optimum for the wash performance of the enzyme so that it approaches the pH of the wash liquor improves the wash performance of the enzyme.

C:

The wash performance of various mutants was tested against grass juice stained cotton cloths according to the method described in Assay A.

2.0 g/l of a liquid detergent (Detergent D3) was used. The detergent was dissolved in ion-exchanged water. The pH was adjusted to 9.1 with NaOH/HCl.

The temperature was kept at 20° C. isothermic for 10 min.

The mutants were dosed at 0.25; 0.5; 1.0; 2.0; 5.0 and 10.0 mg enzyme protein/l each.

The stability of the mutants was determined by measuring the denaturation temperature (maximum excess heat capacity) by differential scanning calorimetry, DSC. The heating rate was 0.5° C./min.

The stability was tested in a solution containing approx. 2 mg/ml of the mutant in 91% standard liquid detergent, the composition of which is described in Assay A. The solution was made by mixing 100 μl of enzyme solution (approx. 20 mg enzyme/ml in a buffer of 0.01 M dimethylglutaric acid, 0.002 M CaCl$_2$, 0.2 M H$_3$BO$_3$ and 0–0.1 M NaCl pH 6.5) with 1000 μl standard liquid detergent.

Within the group of Subtilisin 309, mutants stability results obtained by DSC are consistent with stability results obtained by traditional storage stability tests.

Results:

The wash performance of various mutants in liquid detergent is presented in Table VII. The results are shown as improvement factors relative to the wild type parent enzyme. The improvement factor is defined as in Assay C.

Also shown in Table VII is the denaturation temperature in standard liquid detergent by DSC and the difference between the denaturation temperature of the wild type patent enzyme and that of the mutant in question.

Table VII

| mutant | pI$_o$ calcu- lated | improve- ment factor | Denaturation temperature by DSC | Denaturation temperature by DSC rela- tive to S000 |
| --- | --- | --- | --- | --- |
| S000 | 10.06 | 1 | 65.2 | 0.0 |
| S020 | 7.30 | 7.6 | 58.2 | −7.0 |
| S021 | 9.85 | 1.3 | 69.2 | +4.0 |
| S022 | 8.07 | 9.3 | 61.9 | −3.3 |
| S023 | 8.05 | 8.8 | 63.5 | −1.7 |
| S024 | 6.86 | 3.9 | 60.6 | −4.6 |
| S025 | 8.94 | 6.7 | 69.1 | +3.9 |

Table VII-continued

| mutant | pI₀ calculated | improvement factor | Denaturation temperature by DSC | Denaturation temperature by DSC relative to S000 |
|---|---|---|---|---|
| S035 | 8.07 | 7.0 | 72.5 | +7.3 |
| S201 | 9.85 | 1.4 | 69.4 | +4.2 |

From Table VII it is seen that all of the tested mutants exhibit improved wash performance compared to the wild type parent enzyme. The best wash performance is achieved by the mutants having $pI_o$ equal to or just below the pH of the wash solution.

Denaturation temperature by DSC shows that the stability of the single mutants S021 (*36D) and S201 (N76D) is increased by 4.0° C. and 4.2° C. respectively relative to the wild type parent enzyme.

Among the mutations that are incorporated in one or more of the mutants listed in Table VII, it has been shown that the mutations R170Y and K251E destabilize the mutant relative to the wild type parent enzyme, whereas the mutations H120D, G195E and K235L is indifferent with respect to stability.

It is seen from Table VII that mutants containing one destabilizing mutation are destabilized, even in cases, where a stabilizing mutation is included.

The stabilizing effects of *36D and N76D are additive. This is shown by the mutants S025 and S035. S025 contains three mutations which are indifferent to stability and the stabilizing mutation *36D. The denaturation temperature for S025 is increased by 3.9° C. relative to the wild type parent enzyme, which is equal to the increase measured for the single mutant *36D, S021. S035 contains the same mutation N76D. The denaturation temperature for S035 is increased by 7.3° C. relative to the wild type parent enzyme, which, within experimental error, is equal to the sum of the increase measured for the single mutants *36D, S021 and N76D, S201.

D:
The wash performance of three mutants was tested against grass juice stained cotton cloth according to the method described in Assay A.

2.0 g/l of liquid detergent D3 was used. The detergent was dissolved in ion-exchanged water. The pH was adjusted to 9.1 with NaOH/HCl.

The temperature was kept at 30° C. isothermic for 10 min. The mutants were dosed at 1.0 and 10.0 mg enzyme protein/l each.

Results:
The wash performance of three mutants in commercial US-liquid detergent was tested against grass juice. The results are shown in Table VIII.

TABLE VIII

| | calculated | Delta R values: Enzyme concentration | |
|---|---|---|---|
| Mutant | pI₀ | 1.0 mg/l | 10.0 mg/l |
| S000 | 10.06 | 4.5 | 13.6 |
| S003 | 9.75 | 9.4 | 18.0 |
| S004 | 9.54 | 13.7 | 18.1 |
| S006 | 9.85 | 6.0 | 15.6 |

From Table VIII it is seen that all of the mutants exhibit improved wash performance relative to the wild type parent enzyme. It is further seen that the best performance is achieved by the mutant having $PI_o$ closest to the pH of the wash solution.

E:
The wash performance of two mutants was tested against grass juice stained cotton cloth according to the conditions described in Example D.

Results
The wash performance of two mutants in detergent D3 was tested against grass juice stained cotton cloth. The results are shown in Table IX.

TABLE IX

| | calculated | Delta R values: Enzyme concentration | |
|---|---|---|---|
| Mutant | pI₀ | 1.0 mg/l | 10.0 mg/l |
| S000 | 10.06 | 5.8 | 15.3 |
| S015 | 9.95 | 8.4 | 20.0 |
| S017 | 9.40 | 17.0 | 20.8 |

From Table IX it is seen that all of the mutants exhibit improved wash performance relative to the wild type parent enzyme. It is further seen that the best performance is achieved by the mutant having $pI_o$ closest to the pH of the wash solution.

F:
The wash performance of various mutants was tested on grass juice stained cotton cloth according to the method described in Assay A.

2.0 g/l of detergent D3 was used.

The detergent was dissolved in buffer (0.0025 M Boric acid and 0.001 M disodium hydrogen phosphate prepared in ion exchanged water). The pH was adjusted to 7.0, 8.0, 9.0 and 10.0 respectively with NaOH/HCl. The temperature was kept at 30° C. isothermic for 10 min.

The mutants were dosed at 0.2 mg enzyme protein/l each.
Results:
The wash performance of some of the enzyme variants of the invention at various pH values in a model system are shown in table X.

TABLE X

| Variant | Mutation | pI₀ | Delta R pH | | | |
|---|---|---|---|---|---|---|
| | | | 7.0 | 8.0 | 9.0 | 10.0 |
| S000 | | 10.06 | 0.6 | 0.8 | 4.4 | 7.0 |
| S015 | K235L | 9.95 | 1.3 | 2.4 | 6.0 | 8.8 |
| S021 | *36D | 9.85 | 2.1 | 3.2 | 5.6 | 8.3 |
| S017 | H120D,G195E,K235L | 9.40 | 2.9 | 5.4 | 10.8 | 14.1 |
| S025 | *36D,H120D,R170Y,K235L | 8.95 | 4.3 | 9.5 | 13.9 | 13.1 |
| S023 | *36D,H120D,R170Y,G195E,K235L | 8.05 | 9.6 | 13.0 | 12.4 | 9.2 |
| S024 | *36D,H120D,R170Y,G195E,K235L,K251E | 6.86 | 9.4 | 10.4 | 6.7 | 4.8 |

The results in Table X clearly show that shifting the $pI_o$ of a protease towards the pH of the wash liquor improves the wash performance of the protease.

The results also show that all variants tested have improved performance compared to the wild type parent enzyme at pH below 10.0.

G:
The wash performance of various mutants was tested on grass juice stained cotton cloths according to the method described in Assay A.

2.0 g/l of liquid detergent D3 was used. The detergent was dissolved in 0.005 M glycine prepared in ion-exchanged water). The pH was adjusted to 10.0, 10.25, 10.50, 10.75, 11.0, 11.5 and 12.0, respectively, with NaOH. The temperature was kept at 30° C. isothermic for 10 minutes.

The mutants were dosed at 0.2 mg enzyme protein/l each.
Results:

The wash performance of some of the enzyme variants of the invention at various pH values in a model system are shown in table XI. In this case variants with slightly higher $PI_o$ than the wild type parent enzyme was investigated. The pH range from 10.0 to 12.0 is investigated in more details than in prior examples.

TABLE XI

| Variant | Mutation | $pI_o$ | Delta R pH 10.0 | 10.25 | 10.50 |
|---|---|---|---|---|---|
| S000 |  | 10.06 | 7.0 | 8.7 | 10.5 |
| S027 | E89S | 10.28 | 6.0 | 8.5 | 9.8 |
| S028 | D181N | 10.28 | 6.9 | 9.8 | 10.6 |
| S032 | D197N | 10.28 | 4.7 | 9.2 | 10.8 |
| S033 | E271Q | 10.28 | 7.1 | 6.7 | 7.8 |
| S031 | D197N,E271Q | 10.53 | 4.7 | 7.2 | 7.0 |

| Variant | Mutation | $pI_o$ | Delta R pH 10.75 | 11.0 | 11.5 | 12.0 |
|---|---|---|---|---|---|---|
| S000 |  | 10.06 | 12.5 | 14.4 | 10.6 | 3.8 |
| S027 | E89S | 10.28 | 11.9 | 14.3 | 12.8 | 5.0 |
| S028 | D181N | 10.28 | 13.0 | 14.4 | 10.7 | 4.6 |
| S032 | D197N | 10.28 | 13.8 | 13.5 | 11.3 | 5.0 |
| S033 | E271Q | 10.28 | 10.4 | 13.7 | 13.3 | 6.3 |
| S031 | D197N,E271Q | 10.53 | 10.7 | 13.0 | 14.4 | 8.7 |

The data in Table XI show that at high pH values maximum performance is achieved at pH values a little above the calculated $pI_o$. Still increasing the $pI_o$ of the protease tends to increase the pH of maximum performance. The effects are not as pronounced as it is seen at low pH values (assay B and G).

Figure 5:
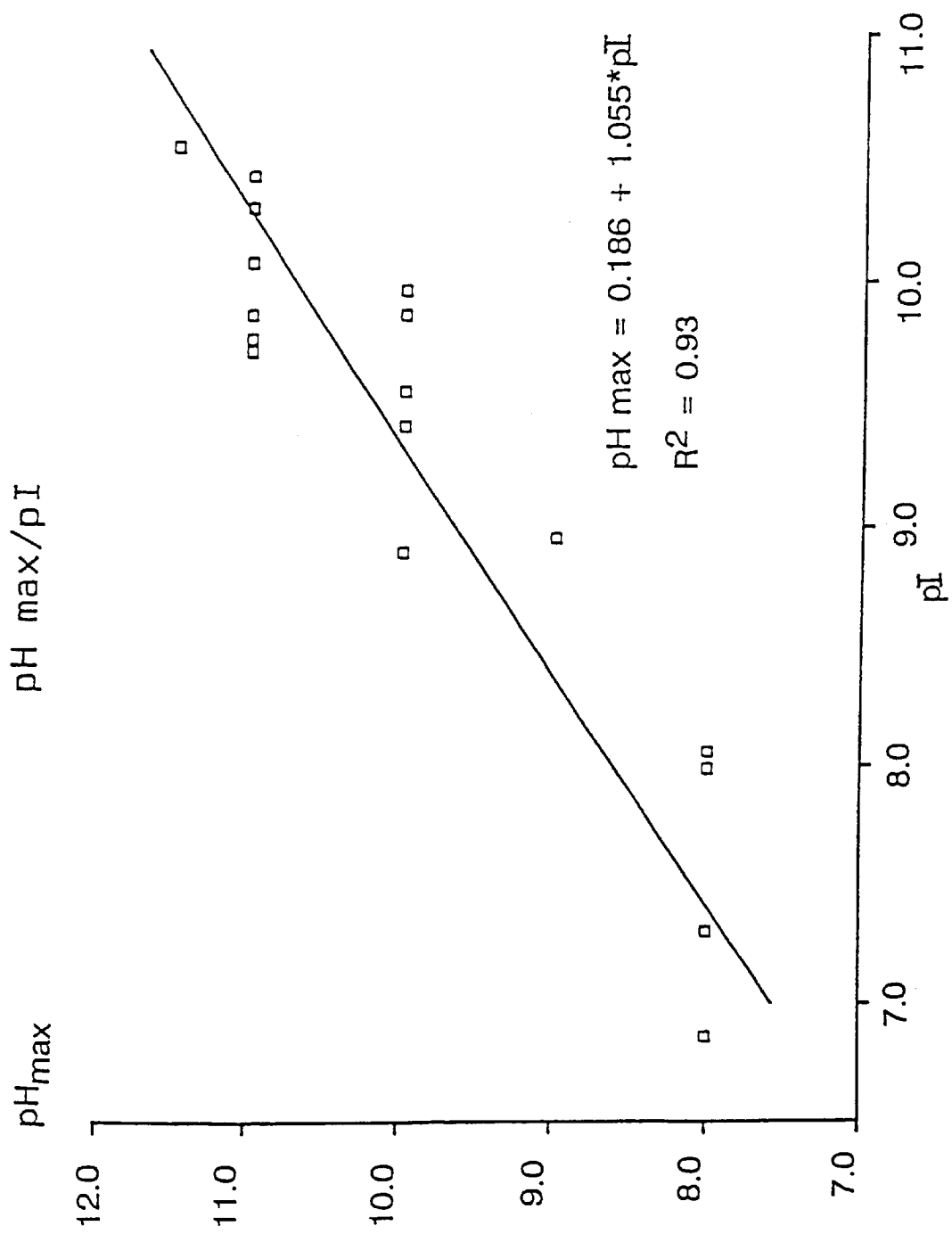
FIG. 5 graphically demonstrates the relationship between pH of maximum performance and calculated pI of the mutant enzymes of the invention.

H:

In order to visualize the correlation between isoelectric point of the protease and the pH at which the protease has its maximum performance, the results from examples B, F and G are used to find the pH at which each of the investigated variants (and the wild type parent enzyme) has its maximum performance. In FIG. 5 this $pH_{max}$ is shown as a function of the calculated $pI_0$.

Taking into account that the pH range is investigated in steps of 1.0 pH value the correlation is obvious.

Concerning the combination of the mutants of the invention with lipase experimental results led to the following practical conclusions:

Lipase was stable for an hour in wash liquor of type O at 37° C. The presence of Savinase® led to rapid deactivation. Kazusase® led to substantially less inactivation of lipase over the period of the test.

Proteinase K was seen to be less aggressive to lipase than Savinase®, but more so than Kazusase®. Subtilisin BPN' did not however inactivate lipase at all under these conditions.

Preferred proteases for use e.g. in connection with lipase in wash compositions represented by type O, are mutants S001, S003, S004, S012, S019, S020, S021, S025, S035 and S235.

Type O wash liquor was a 5 g/l solution at 37° C. derived from the following detergent formulation (% by wt):

| | |
|---|---|
| anionic surfactant | 6 |
| nonionic surfactant | 5 |

-continued

| | |
|---|---|
| fatty acid | 2.8 |
| acrylic polymer | 3 |
| zeolite | 22 |
| carbonate | 10 |
| sulphate | 17.5 |
| clay | 8 |
| tertiary amine | 2 |
| perborate monohydrate | 13 |
| minors and water | to 100. |

Preferred proteases for use in connection with lipase in wash compositions represented by type W are mutant S020, S021, S025, S035 and S235.

Type W wash liquor was a 2 g/l solution of a liquid detergent having the following formulation (% by wt):

| | |
|---|---|
| anionic surfactant | 16 |
| nonionic surfactant | 7 |
| hydrotrope | 6 |
| citric acid | 6.5 |
| NaOH | 4.1 |
| monoethanolamine | 2 |
| minors and water | to 100. |

Detergent compositions Comprising Lipase

Experimental tests of lipase stability were carried out for example using the following materials:

1 LU/ml Pseudomonas cepacia lipase was incubated in wash liquor of each of two types, O and W (described below). Aliquots were taken at intervals and tested for lipase activity. Parallel incubations were carried out without protease or with protease on the retention of lipase activity. Wild-type proteases were tested at 20 GU/ml, mutated proteases were tested at 015 microgram/ml.

Experimental results led to the following conclusions:

Lipase was stable for an hour in wash liquor of type 0 at 37° C. The presence of Savinase™ led to rapid deactivation. Kazusase™ led to substantially less inactivation of lipase over the period of the test.

Proteinase K was seen to be less aggressive to lipase than Savinase, but more so than Kazusase. Subtilisin BPN' did not however inactivate lipase at all under these conditions.

Preferred proteases for use e.g. in connection with lipase in wash compositions represented by type O, are Mutants S001, S003, S004, S012, S019 and S020.

Type O wash liquor was a 5 g/l solution at 37° C. derived from the following detergent formulation (wt %):

| | |
|---|---|
| anionic surfactant | 6 |
| nonionic surfactant | 5 |
| fatty acid | 2.8 |
| acrylic polymer | 3 |
| zeolite | 22 |
| carbonate | 10 |
| sulphate | 17.5 |
| clay | 8 |
| tertiary amine | 2 |
| perborate monohydrate | 13 |
| minors and water | to 100. |

A preferred protease for use e.g. in connection with lipase in wash compositions represented by type W is example S020. Type W wash liquor was a 2 g/l solution of a liquid detergent having the following formulation (wt %):

| | |
|---|---|
| anionic surfactant | 16 |
| nonionic surfactant | 7 |
| hydrotrope | 6 |
| citric acid | 6.5 |
| NaOH | 4.1 |
| monoethanolamine | 2 |
| minors and water | to 100. |

The invention is illustrated by way of the following non-limiting Examples:

Example 1L

A detergent powder is formulated to contain: total active detergent about 16%, anionic detergent about 9%, nonionic detergent about 6%, phosphate-containing builder about 20%, acrylic or equivalent polymer about 3.5%, perborate or peracid bleach precursor about 6–18%, amino-containing bleach activator about 2%, silicate or other structurant about 3.5%, protease enzyme about 8 glycine units/mg, with alkali to adjust to desired pH in use, and neutral inorganic salt, and enzymes (about 0.5% each protease and lipase).

The anionic detergent is a mixture of sodium dodecylbenzene sulphonate 6% and primary alkyl sulphate 3%. The nonionic detergent is an ethoxylate of an approx. C13–C15 primary alcohol with 7 ethoxylate residues per mole. The phosphate builder is sodium tripolyphosphate. The polymer is polyacrylic acid. The perborate or peracid bleach precursor is sodium tetraborate tetrahydrate or monohydrate. The activator is tetraacetylethylenediamine. The structurant is sodium silicate. The neutral inorganic salt is sodium sulphate. The enzymes comprise lipase and Mutant S001 as the protease. Alternatively, the protease enzyme is selected from S003, S004, C002, C003 and C004.

Example 2L

A detergent powder is formulated to contain: total active detergent about 16%, anionic detergent about 9%, nonionic detergent about 6%, zeolite-containing builder about 20%, acrylic or equivalent polymer about 3.5%, perborate or peracid bleach precursor about 6–18%, amino-containing bleach activator about 2%, silicate or other structurant about 3.5%, protease enzyme about 8 glycine units/mg, with alkali to adjust to desired pH in use, and neutral inorganic salt, and enzymes (about 0.5% each of protease and lipase enzyme).

The anionic detergent is a mixture of sodium dodecylbenzene sulphonate 6% and primary alkyl sulphate 3%. The nonionic detergent is an ethoxylate of an approx. C13–C15 primary alcohol with 7 ethoxylate residues per mole. The zeolite builder is type A zeolite. The polymer is polyacrylic acid. The perborate bleach precursor is sodium tetraborate tetrahydrate or monohydrate. The activator is tetraacetylethylenediamine. The structurant is sodium silicate. The neutral inorganic salt is sodium sulphate. The protease enzyme is Mutant S001. Alternatively, the enzyme is selected from S003, S004, C002, C003 and C004. Lipase and protease are both present at about 0.5%.

Example 3L

An aqueous detergent liquid is formulated to contain: Dodecylbenzene-sulphonic acid 16%, C12–C15 linear alcohol condensed with 7 mol/mol ethylene oxide 7%, monoethanolamine 2%, citric acid 6.5%, sodium xylenesulphonate 6%, sodium hydroxide about 4.1%, protease 0.5%, minors and water to 100%. The pH is adjusted to a value between 9 and 10. The protease enzyme is Mutant S0020. Alternatively, the protease enzyme is selected from S0019, S0012, S001, S003 and S004. Lipase and protease are both present at about 0.5%.

Example 4L

A nonaqueous detergent liquid is formulated using 38.5% C13–C15 linear primary alcohol alkoxylated with 4.9 mol/mol ethylene oxide and 2.7 mol/mol propylene oxide, 5% triacetin, 30% sodium triphosphate, 4% soda ash, 15.5% sodium perborate monohydrate containing a minor proportion of oxoborate, 4% TAED, 0.25% EDTA of which 0.1% as phosphonic acid, Aerosol 0.6%, SCMC 1%, and 0.6% protease. The pH is adjusted to a value between 9 and 10, e.g. about 9.8. The protease enzyme is Mutant S001, S003 or S004. Lipase and protease are both present at about 0.5%.

Example 5L

A detergent powder is formulated in the form of a granulate having a bulk density of at least 600 g/l, containing about 20% by weight surfactant of which about 10% is sodium dodecylbenzene sulphonate, and the remainder is a mixture of Synperonic A7 and Synperonic A3 (about 5.5% to 4.5%), and zero neutral inorganic salt (e.g. sodium sulphate), plus phosphate builder about 33%, sodium perborate tetrahydrate about 16%, TAED activator about 4.5%, sodium silicate about 6%, and minors including sodium carbonate about 2%, and moisture content about 10%. Enzymes (about 0.5% each of lipase and protease enzyme) are included. The protease enzyme is Mutant S001. Alternatively, the protease enzyme is selected from S003, S004, C002, C003 and C004.

Example 6L

A detergent powder is formulated in the form of a granulate having a bulk density of at least 600 g/l, containing about 20% by weight surfactant of which about 9% is sodium dodecylbenzene sulphonate, and the remainder is a mixture of Synperonic A7 and Synperonic A3 (respectively about 5% and 6%), and zero neutral inorganic salt (e.g. sodium sulphate), plus zeolite builder about 30%, sodium perborate tetrahydrate about 14%, TAED activator about 3.6%, and minors including sodium carbonate about 9%, Dequest 2047™ about 0.7%, and moisture content about 10%. Enzymes (about 0.5% each of lipase and protease enzyme) are included. The protease enzyme is Mutant S001. Alternatively, the protease enzyme is selected from S003, S004, C002, C003 and C004.

Example 7L

A detergent powder is formulated to contain: Dodecylbenzenesulphonic acid 6%, C12–C15 linear alcohol condensed with 7 mol/mol ethylene oxide 5%, fatty acid soap 3%, Sokolan CP5 polymer™ 3%, zeolite A 22%, sodium carbonate 10%, sodium sulphate 17%, clay particles 8%, sodium perborate tetrahydrate 13%, tetraacetylethylenediamine 2%, protease 0.5%, minors and water to 100%. The pH is adjusted to a value between 9 and 10. The protease enzyme is Mutant S020. Alternatively, the enzyme is selected from S019, S012, S004, S001 and S003. Lipase and protease are both present at about 0.5%.

Example 8L

A detergent (soap) bar is formulated as follows: soap based on pan-saponified 82% tallow, 18% coconut oil, neutralized with 0.15% orthophosphoric acid, mixed with protease (about 8 GU/mg of the bar composition) and with sodium formate 2%, borax 2%, propylene glycol 2% and sodium sulphate 1%, is then plodded on a soap production line. The protease enzyme is Mutant S001. Alternatively, the protease is selected from S003, S004, C002, C003 and C004. Lipase and protease are both present at about 0.5%.

In further embodiments of the invention, structured liquid detergents can further contain e.g. 2–15% nonionic surfactant, 5–40% total surfactant, comprising nonionic and optionally anionic surfactant, 5–35% phosphate-containing or non-phosphate-containing builder, 0.2–0.8% polymeric thickener, e.g. cross-linked acrylic polymer with m.w. over $10^6$, at least 10% sodium silicate, e.g. as neutral waterglass, alkali (e.g. potassium-containing alkali) to adjust to desired pH, preferably in the range 9–10 or upwards, e.g. about pH 11, with a ratio sodium cation: silicate anion (as free silica) (by weight) less than 0.7:1, and viscosity of 0.3–30 Pa.s (at 20° C. and 20 reciprocal secs).

For example, such detergents can contain about 5% nonionic surfactant C13–15 alcohol alkoxylated with about 5 EO groups and about 2.7 PO groups per mole, 15–23% neutral waterglass with 3.5 weight ratio between silica and sodium oxide, 13–19% KOH, 8–23% STPP, 0–11% sodium carbonate, 0.5% Carbopol 941™. Protease may be incorporated at for example 0.5% of Mutant S001.

Although the present invention has been discussed and exemplified in connection with various specific embodiments thereof this is not to be construed as a limitation to the applicability and scope of the disclosure, which extends to all combinations and subcombinations of features mentioned and described in the foregoing as well as in the attached patent claims.

What is claimed is:

1. A modified subtilisin comprising a substitution of an amino acid with a different amino acid at one or more positions selected from the group consisting of:
   27, 105, 106, 141, 251, 256, and 257,
wherein each position corresponds to the position of the amino acid sequence of the mature subtilisin BPN'.

2. The modified subtilisin of claim 1, which comprises a substitution at position 27.

3. The modified subtilisin of claim 1, which comprises a substitution at position 105.

4. The modified subtilisin of claim 1, which comprises a substitution at position 106.

5. The modified subtilisin of claim 1, which comprises a substitution at position 141.

6. The modified subtilisin of claim 1, which comprises a substitution at position 251.

7. The modified subtilisin of claim 1, which comprises a substitution at position 256.

8. The modified subtilisin of claim 1, which comprises a substitution at position 257.

9. The modified subtilisin of claim 1, wherein the subtilisin that is modified is selected from the group consisting of subtilisin BPN', subtilisin amylosacchariticus, subtilisin 168, subtilisin mesentericopeptidase, subtilisin Carlsberg, subtilisin DY, subtilisin 309, subtilisin 147, thermitase, aqualysin, Bacillus PB92 protease, proteinase K, Protease TW7 and Protease TW3.

10. The modified subtilisin of claim 9, wherein the subtilisin that is modified is subtilisin 309.

11. The modified subtilisin of claim 1, which has a net electrostatic charge that is different from that of the parent subtilisin at the same pH and has an isoelectric point that is higher or lower than that of the parent subtilisin.

12. The modified subtilisin of claim 11, which has a net electrostatic charge that is more positive than that of the parent subtilisin.

13. The modified subtilisin of claim 11, which has a net electrostatic charge that is more negative than that of the parent subtilisin.

14. The modified subtilisin of claim 1, which has at least one different amino acid that is more positive than the amino acid in the corresponding position in the parent subtilisin.

15. The modified subtilisin of claim 1, which has at least one different amino acid that is more negative than the amino acid in the corresponding position of the parent subtilisin.

16. A detergent composition comprising a modified subtilisin of claim 1 and a surfactant.

17. A modified subtilisin comprising an insertion of an amino acid at position 36, wherein position 36 corresponds to the position of the amino acid sequence of the mature subtilisin BPN'.

18. The modified subtilisin of claim 17, wherein the amino acid is a negatively charged amino acid.

19. The modified subtilisin of claim 18, wherein the amino acid is D or E.

20. The modified subtilisin of claim 17, wherein the amino acid is a neutral or positively (harged amino acid.

21. The modified subtilisin of claim 20, wherein the amino acid is A, K, N, Q, or R.

22. A detergent composition comprising a modified subtilisin of claim 17 and a surfactant.

23. A modified subtilisin comprising a mutation in an amino acid sequence of a subtilisin at a position numbered according to the amino acid sequence of the mature subtilisin BPN', wherein the mutation is selected from the group consisting of:
   Q12K, Q12R, R19Q, T22R, D32*, T38K, T38R, R45A, E53G+K235L, E53K, E53R, E54G, E54T, E54Y, Q59E, T71D, T71D+G195E, E89S, G97D, G97D+H120K, N97D, N97D+S98D, N97D+T213D, A98K, A98R, S98D, S98D+T213D, S99D, S99D+N140K, D120K, H120D+G195E, H120D+G195E+K235L+K251E, H120D+R170Y+G195E+K235L+K251E, H120K, P129D, D140K, N140K, N140R, S156E, A158K, A158R, Y167V, R170Y+K251E, Y171T, D172K, R186P G195E+T213R, G195F, D197E, D197K, D197N, Q206D, Q206E, T213D, Y214S, Y214T, K235L, K235R, K237R, W241L, and S265R.

24. A modified subtilisin of claim 23, wherein the mutation comprises Q12K.

25. A modified subtilisin of claim 23, wherein the mutation comprises Q12R.

26. A modified subtilisin of claim 23, wherein the mutation comprises R19Q.

27. A modified subtilisin of claim 23, wherein the mutation comprises T22R.

28. A modified subtilisin of claim 23, wherein the mutation comprises D32*.

29. A modified subtilisin of claim 23, wherein the mutation comprises T38K.

30. A modified subtilisin of claim 23, wherein the mutation comprises T38R.

31. A modified subtilisin of claim 23, wherein the mutation comprises R45A.

32. A modified subtilisin of claim 23, wherein in the mutation comprises E53G+K235L.

33. A modified subtilisin of claim 23, wherein the mutation comprises E53K.

34. A modified subtilisin of claim 23, wherein the mutation comprises E53R.

35. A modified subtilisin of claim 23, wherein the mutation comprises E54G.

36. A modified subtilisin of claim 23, wherein the mutation comprises E54T.

37. A modified subtilisin of claim 23, wherein the mutation comprises E54Y.

38. A modified subtilisin of claim 23, wherein the mutation comprises E59E.

39. A modified subtilisin of claim 23, wherein the mutation comprises T71D.

40. A modified subtilisin of claim 23, wherein the mutation comprises T71D+G195E.

41. A modified subtilisin of claim 23, wherein the mutation comprises E89S.

42. A modified subtilisin of claim 23, wherein the mutation comprises G97D.

43. A modified subtilisin of claim 23, wherein the mutation comprises G97D+H120K.

44. A modified subtilisin of claim 23, wherein the mutation comprises N97D.

45. A modified subtilisin of claim 23, wherein the mutation comprises N97D+S98D.

46. A modified subtilisin of claim 23, wherein the mutation comprises N97D+T213D.

47. A modified subtilisin of claim 23, wherein the mutation comprises A98K.

48. A modified subtilisin of claim 23, wherein the mutation comprises A98R.

49. A modified subtilisin of claim 23, wherein the mutation comprises S98D.

50. A modified subtilisin of claim 23, wherein the mutation comprises S98D+T213D.

51. A modified subtilisin of claim 23, wherein the mutation comprises S99D.

52. A modified subtilisin of claim 23, wherein the mutation comprises S99D+N140K.

53. A modified subtilisin of claim 23, wherein the mutation comprises D120K.

54. A modified subtilisin of claim 23, wherein the mutation comprises H120+G195E.

55. A modified subtilisin of claim 23, wherein the mutation comprises H120D+R195E+K235L+K251E.

56. A modified subtilisin of claim 23, wherein the mutation comprises H120D+R170Y+G195E+K235L+K251E.

57. A modified subtilisin of claim 23, wherein the mutation comprises N120K.

58. A modified subtilisin of claim 23, wherein the mutation comprises P129D.

59. A modified subtilisin of claim 23, wherein the mutation comprises D140K.

60. A modified subtilisin of claim 23, wherein the mutation comprises N140K.

61. A modified subtilisin of claim 23, wherein the mutation comprises N140R.

62. A modified subtilisin of claim 23, wherein the mutation comprises S156E.

63. A modified subtilisin of claim 23, wherein the mutation comprises A158K.

64. A modified subtilisin of claim 23, wherein the mutation comprises A158R.

65. A modified subtilisin of claim 23, wherein the mutation comprises Y167V.

66. A modified subtilisin of claim 23, wherein the mutation comprises R170Y+K251E.

67. A modified subtilisin of claim 23, wherein the mutation comprises R171T.

68. A modified subtilisin of claim 23, wherein the mutation comprises D172K.

69. A modified subtilisin of claim 23, wherein the mutation comprises D186P.

70. A modified subtilisin of claim 23, wherein the mutation comprises G195E+T213R.

71. A modified subtilisin of claim 23, wherein the mutation comprises G195F.

72. A modified subtilisin of claim 23, wherein the mutation comprises G197E.

73. A modified subtilisin of claim 23, wherein the mutation comprises D197K.

74. A modified subtilisin of claim 23, wherein the mutation comprises D197N.

75. A modified subtilisin of claim 23, wherein the mutation comprises Q206D.

76. A modified subtilisin of claim 23, wherein the mutation comprises Q206E.

77. A modified subtilisin of claim 23, wherein the mutation comprises T213D.

78. A modified subtilisin of claim 23, wherein the mutation comprises Y214S.

79. A modified subtilisin of claim 23, wherein the mutation comprises Y214T.

80. A modified subtilisin of claim 23, wherein the mutation comprises K235L.

81. A modified subtilisin of claim 23, wherein the mutation comprises K235R.

82. A modified subtilisin of claim 23, wherein the mutation comprises K237R.

83. A modified subtilisin of claim 23, wherein the mutation comprises K241L.

84. A modified subtilisin of claim 23, wherein the mutation comprises S265R.

85. The modified subtilisin of claim 23, wherein the subtilisin that is modified is selected from the group consisting of subtilisin BPN', subtilisin amylosacchariticus, subtilisin 168, subtilisin mesentericopeptidase, subtilisin Carlsberg, subtilisin DY, subtilisin 309, subtilisin 147, thermitase, aqualysin, Bacillus PB92 protease, proteinase K, Protease TW7 and Protease TW3.

86. The modified subtilisin of claim 85, wherein the subtilisin that is modified is subtilisin 309.

87. A detergent composition comprising a modified subtilisin of claim 23 and a surfactant.

* * * * *